US006912424B2

(12) United States Patent
Bishay et al.

(10) Patent No.: US 6,912,424 B2
(45) Date of Patent: Jun. 28, 2005

(54) APPARATUS AND METHOD FOR COUPLING THERAPEUTIC AND/OR MONITORING EQUIPMENT TO A PATIENT

(75) Inventors: Jon M. Bishay, Woodinville, WA (US); Paul C. Leonard, Woodinville, WA (US); Jay M. Miazga, Seattle, WA (US)

(73) Assignee: Meagan, Medical, Inc., Reno, NV (US)

( * ) Notice: Subject to any disclaimer, the term of this patent is extended or adjusted under 35 U.S.C. 154(b) by 219 days.

(21) Appl. No.: 09/751,382

(22) Filed: Dec. 29, 2000

(65) Prior Publication Data

US 2001/0021869 A1 Sep. 13, 2001

Related U.S. Application Data

(63) Continuation-in-part of application No. 09/452,477, filed on Dec. 1, 1999, now Pat. No. 6,622,051, and a continuation-in-part of application No. 09/666,931, filed on Sep. 21, 2000, now Pat. No. 6,529,776.

(51) Int. Cl.$^7$ ................................................. A61N 1/02

(52) U.S. Cl. ........................................ 607/46; 607/115

(58) Field of Search ............................ 607/1, 2, 46, 48, 607/50, 115, 116, 152, 148, 149; 600/382, 386, 390, 393, 394

(56) References Cited

U.S. PATENT DOCUMENTS

| 3,030,959 A | 4/1962 | Grunert |
| 3,090,151 A | 5/1963 | Stewart et al. |
| 3,208,452 A | 9/1965 | Stern |

(Continued)

FOREIGN PATENT DOCUMENTS

| FR | 2500309 | 8/1982 |
| FR | 2 500 745 | 9/1982 |
| GB | 2 163 355 A | 2/1986 |
| WO | WO 01/39829 A1 | 6/2001 |

OTHER PUBLICATIONS

Association for Advancement of Medical Instrumentation, "Implantable Peripheral Nerve Stimulators," American National Standard, ANSI/AAMI NS15—1995 pp. 1–8 NS15—1995 pp. 1–8.

Ahmed H. et al. "Percutaneous Electrical Nerve Stimulation (PENS): A Complementary Therapy for the Management of Paln Secondary to Bony Metastasis", The Clinical Journal of Paln (Dec. 1998) vol. 14, No. 4, pp. 320–323, Lippincott Williams & Wilkins, Philadelphia.

Ahmed H. et al. "Percutaneous Electrical Nerve Stimulation: An Alternative to Antiviral Drugs for Acute Herpes Zoster," Anesthesia & Analgesia (Oct. 1998) 87: 911–4.

(Continued)

*Primary Examiner*—George R. Evanisko
(74) *Attorney, Agent, or Firm*—Blank Rome LLP

(57) ABSTRACT

A method and apparatus for supporting couplers for therapy administration and/or monitoring. The apparatus can include a support member configured to rest on a body of a recipient proximate to a coupling area. The support member can include a first coupler location configured to removably carry a first coupler proximate to a first coupling position of the body of the recipient. A second coupler location of the support member is configured to removably carry a second coupler proximate to a second coupling position of the body of the recipient. The first and second coupler locations can be arranged to guide the practitioner to connect the couplers properly to the body. For example, the first coupler location can be positioned closer than the second coupler location to the first coupling position. Accordingly, practitioners can be more likely to connect the first and second couplers to the correct coupling position on the body of the recipient.

13 Claims, 17 Drawing Sheets

U.S. PATENT DOCUMENTS

| | | | |
|---|---|---|---|
| 3,938,526 A | | 2/1976 | Anderson et al. |
| 3,943,935 A | | 3/1976 | Cameron |
| 3,983,881 A | | 10/1976 | Wickham |
| 4,139,011 A | | 2/1979 | Benoit et al. |
| 4,153,059 A | | 5/1979 | Fravel et al. |
| 4,207,903 A | | 6/1980 | O'Neill |
| 4,256,116 A | | 3/1981 | Meretsky et al. |
| 4,262,672 A | | 4/1981 | Kief |
| 4,281,659 A | | 8/1981 | Farrar et al. |
| 4,284,856 A | | 8/1981 | Hochmair et al. |
| 4,381,012 A | * | 4/1983 | Russek ............ 600/382 |
| 4,408,617 A | | 10/1983 | Auguste |
| 4,431,000 A | | 2/1984 | Butler et al. |
| 4,437,467 A | | 3/1984 | Helfer et al. |
| 4,512,351 A | | 4/1985 | Pohndorf |
| 4,541,432 A | | 9/1985 | Molina-Negro et al. |
| 4,556,064 A | | 12/1985 | Pomeranz et al. |
| 4,583,549 A | | 4/1986 | Manoli |
| 4,685,466 A | | 8/1987 | Rau |
| 4,686,996 A | | 8/1987 | Ulbrich |
| 4,712,558 A | | 12/1987 | Kidd et al. |
| D297,047 S | | 8/1988 | Hon et al. |
| 4,765,310 A | | 8/1988 | Deagle et al. |
| 4,895,154 A | | 1/1990 | Bartelt et al. |
| 4,934,371 A | | 6/1990 | Malis et al. |
| 4,949,734 A | | 8/1990 | Bernstein |
| 4,953,564 A | | 9/1990 | Berthelsen |
| 4,979,508 A | | 12/1990 | Beck |
| 5,012,811 A | | 5/1991 | Malis et al. |
| D318,330 S | | 7/1991 | Doty et al. |
| 5,033,474 A | * | 7/1991 | Varelis et al. ............ 600/509 |
| 5,036,850 A | | 8/1991 | Owens |
| 5,054,486 A | | 10/1991 | Yamada |
| 5,094,242 A | | 3/1992 | Gleason et al. |
| 5,117,826 A | | 6/1992 | Bartelt et al. |
| 5,211,175 A | | 5/1993 | Gleason et al. |
| 5,246,014 A | | 9/1993 | Williams et al. |
| 5,255,691 A | | 10/1993 | Otten |
| 5,269,304 A | | 12/1993 | Matthews |
| 5,281,218 A | | 1/1994 | Imran |
| 5,332,401 A | | 7/1994 | Davey et al. |
| D357,069 S | | 4/1995 | Plahn et al. |
| 5,417,719 A | | 5/1995 | Hull et al. |
| 5,423,314 A | | 6/1995 | Schmid |
| 5,439,440 A | | 8/1995 | Hofmann |
| 5,449,378 A | | 9/1995 | Schouenborg |
| 5,593,429 A | | 1/1997 | Ruff |
| 5,649,936 A | | 7/1997 | Real |
| 5,674,267 A | | 10/1997 | Mir et al. |
| 5,682,233 A | | 10/1997 | Brinda |
| 5,702,359 A | | 12/1997 | Hofmann et al. |
| 5,810,762 A | | 9/1998 | Hofmann |
| 5,851,223 A | | 12/1998 | Liss et al. |
| 5,861,015 A | | 1/1999 | Benja-Athon |
| 5,873,849 A | | 2/1999 | Bernard |
| 5,928,144 A | | 7/1999 | Real |
| 5,941,845 A | | 8/1999 | Tu et al. |
| 5,948,008 A | | 9/1999 | Daikuzono |
| 5,968,011 A | | 10/1999 | Larsen et al. |
| 5,968,063 A | | 10/1999 | Chu et al. |
| 6,009,347 A | | 12/1999 | Hofmann |
| 6,032,064 A | | 2/2000 | Devlin et al. |
| 6,035,236 A | | 3/2000 | Jarding et al. |
| 6,050,992 A | | 4/2000 | Nichols |
| 6,068,650 A | | 5/2000 | Hofmann et al. |
| 6,117,077 A | * | 9/2000 | Del Mar et al. ............ 600/382 |
| 6,122,547 A | | 9/2000 | Benja-Athon |
| 6,208,893 B1 | | 3/2001 | Hofmann |
| 6,219,569 B1 | | 4/2001 | Kelly et al. |
| D443,063 S | | 5/2001 | Pisani et al. |
| 6,269,270 B1 | | 7/2001 | Boveja |
| 6,304,785 B1 | | 10/2001 | McCreery et al. |
| 6,341,237 B1 | | 1/2002 | Hurtado |
| 6,355,021 B1 | | 3/2002 | Nielsen et al. |
| 6,493,592 B1 | | 12/2002 | Leonard et al. |
| 6,516,226 B1 | | 2/2003 | Bishay et al. |
| 6,522,927 B1 | | 2/2003 | Bishay et al. |
| 6,539,264 B1 | | 3/2003 | Bishay et al. |
| 6,549,797 B1 | | 4/2003 | Leonard et al. |
| 6,549,810 B1 | | 4/2003 | Leonard et al. |
| 6,556,869 B1 | | 4/2003 | Leonard et al. |
| 6,560,491 B1 | | 5/2003 | Bishay et al. |

OTHER PUBLICATIONS

Almay, B.G.L. et al., "Long–Term High Frequency Transcutaneous Electrical Nerve Stimulation (hi–TNS) in Chronic Pain. Clinical Response and Effects on CSF Endorphins, Monoamine Metabolites, Substance P–Like Immunoreactivity (SPLI) and Pain Measures," Journal of Psychosomatic Research, (1985) vol. 29, No. 3, pp. 247–257, Pergamon Press Ltd. Great Britain.

Baker, L. L., et al. "Effects of Waveform on Comfort during Neuromuscular Electrical Stimulation," Clinical Orthopaedics and Related Research, Aug. 1998, No. 223, pp. 75–85.

Ballegaard, S. et al. "Acupuncture and Transcutaneous Electric Nerve Stimulation in the Treatment of Pain Associated with Chronic Pancreatitis. A Randomized Study", Scand. J. Gastroenterol. (Jun. 1985) 20: 1249–54.

Balogun, J. et al. "The effects of acupunture, electroneedling and transcutaneous electrical stimulation therapies on peripheral haemodynamic functioning", Disability and Rehabilitation (Feb. 1998) vol. 20, No. 2, pp, 41–48, Taylor & Francis Ltd.

Balogun, J., "Effects of Ramp Time on Sensory, Motor and Tolerance Thresholds during Exogenous Electrical Stimulation," The Journal of Sports Medicine and Physical Fitness, (Dec. 1991) vol. 31, No. 4, pp. 521–526.

BD Microtainer Brand Safety Flow Lancet—Product No. 366356. BD catalog 1997–2000, http://catalog.bd.com/sctipts/OBDsheet.exe?FNC=productlist Alistproducts. html 3 66356 (Aug. 2001), 3 pages.

BD Safety Products. BD Vacutainer Safety–Lok Blood Collection Set; BD Vacutainer SafetyGlide Blood Collection Assembly and BD Vacutainer Eclipse Blood Collection Needle, 1 page.

BD Vacutainer SafetyGlide Blood Collection Assembly. Quick Reference Card (Oct. 1999), 1 page.

Brull, S. J., et al., "Pulse Width, Stimulus Intensity, Electrode Placement, and Polarity during Assessment of Neuromuscular Block," Anesthesiology, (Oct. 1995) V. 83, No. 4, pp. 702–709, Lippincott–Raven Publishers.

Bushnell, M. C. et al. "Electrical stimulation of peripheral and central pathways for the relief of musculoskeletal pain", Can. J. Physiol. Pharmacol. (May 1991) 69: 697703.

Carroll, D. et al., "Randomization is important in Studies with Pain Outcomes; Systematic Review of Transcutaneous Electrical Nerve Stimulation in Acute Postoperative Pain," British Journal of Anesthesiology, (1996) vol. 77, pp. 798–803.

Cassuto, J. et al., "The Use of Modulated Energy Carried on a High Frequency Wave for the Relief of Intractable Pain," International Journal of Clinical Pharm.Research (1993) XI II (4) pp. 239–241.

Cheng R., Pomeranz, B. "Electroacupunture analgesia could be mediated by at least two pain–relieving mechanisms; endorphin and non–endorphin systems", Life Sciences (Dec. 1979) 25: 1957–62, Pergamon Press Ltd.

Cheng R. et al. "Electroacupunture elevates blood cortisol levels in naive horses; sham treatment has no effect", Intern. J. Neuroscience (Feb. 1980) vol. 10, pp. 95–97, Gordon and Breach Science Publishers, Inc., Great Britain.

Cheng R. S. S., Pomeranz, B. "Electrotherapy of Chronic Musculoskeletal Pain: Comparison of Electroacupuncture and Acupuncture–Like Transcutaneous Electrical Nerve Stimulation", The Clinical Journal of Pain (1987) vol. 2, No. 3, pp. 143–149, Raven Press, New York.

Cramp, A.F.L. et al.,"The Effect of High– and Low–Frequency Transcutaneous Electrical Nerve Stimulation Upon Cutaneous Blood Flow and Skin Temperature in Healthy Subjects," Clinical Physiology 20, (2000) 2, pp. 150–157, Blackwell Science Ltd.

Empi Eclipse+ Dual Channel Transcutaneous Electrical Nerve Stimulator User's Manual, Empi, Inc. (Sep. 1998), US patent #D282,968, 31 pages.

Empi EPIX VT Dual Channel Transcutaneous Electrical Nerve Stimulator Instruction Manual, Empi, Inc. (1997) 22 pages.

Empi EPIX XL TENS Instruction Manual, Empi, Inc. (Sep. 1998) U.S. patent No. D319,881, 22 pages.

Empi, Our Products: Electrotherapy for Rehabilitation, http://www.empi.com/b/b2.htm, (Mar. 2001), 8 pages.

Foster, N.E., et al., "Manipulation of Transcutaneous Electrical Nerve Stimulation Variables Has No Effect on Two Models of Experimental Pain in Humans," The Clinical Journal of Pain, (1996) 12; pp. 301–310, Lippincott–Raven Publishers, Philadelphia.

Gadsby, G. et al. "Nerve stimulation for low back pain—a review," Nursing Standard (Jul. 1997) vol. 11, No. 43, pp. 32–33.

Galleti, S.P., et al., "Highlights in the Subject of Low Frequency–High Intensity TENS," Minerva Stomatologica (Italy) (Sep. 1995), 44, pp. 421–429.

Ghoname, E. et al. "Does the Stimulus Frequency Affect the Analgesic Response to Electrical Stimulation?" Anesthesia & Analgesia (Nov. 1999) 88: S210, Lippincott Williams & Wilkins.

Ghoname, E. et al. "Percutaneous Electrical Nerve Stimulation for Low Back Pain", JAMA (Mar. 1999) vol. 281, No. 9, pp. 818–823.

Ghoname, E. et al. "Percutaneous electrical nerve stimulation: an alternative to TENS in the management of sciatica", Pain (Nov. 1999) 83: 193–9, Elsevier Science B.V.

Ghoname, E. et al. "The Effect of Stimulus Frequency on the Analgesic Response to Percutaneous Electrical Nerve Stimulation in Patients with Chronic Low Back Pain", Anesthesia & Analgesia (Oct. 1999) 88: 841–6.

Ghoname, E. et al. "The Effect of the Duration of Electrical Stimulation on the Analgesic Response", Anesthesia & Analgesia (Jan. 1999) 88: S211.

Gopalkrishnan, P., et al., "Effect of Varying Frequency, Intensity, and Pulse Duration of Transcutaneous Electrical Nerve Stimulation on Primary Hyperalgesia in Inflamed Rats," Arch. Phys. Med. Rehabil., (Jul. 2000) vol. 81, pp. 984–990.

Gracanin, F., et al., "Optimal Stimulus Parameters for Minimum Pain in the Chronic Stimulation of Innervated Muscle," Arch. Phys. Med. Rehabil. (Jun. 1975) vol. 56, pp. 243–249.

Hamza, M. et al., "Effect of the Duration of Electrical Stimulation on the Analgesic Response in Patients with Low Back Pain", Anesthesiology (Dec. 1999), vol. 91, No. 6, pp. 1622–1627, Lippincott Williams & Wilkins, Inc.

Hamza, M.A., et al., "Effect of the Frequency of Transcutaneous Electrical Nerve Stimulation on the Postoperative Opioid Angalgesic Requirement and Recovery Profile," Anesthesiology, (Nov. 1999) V. 91, No. 5, pp. 1232–1238.

Han, J.S. et al., "Effect of Low– and High–Frequency TENS on Met–enkephalin–Arg Phe and dynorphin A immunoreactivity in human lumbar CSF," Pain, (1991) vol. 47, pp. 295–298, Elsevier Science Publishers B.V.

Healthronics HANS LY257 User Manual, Healthronics Pte Ltd., Singapore, 15 pages.

Innovative Healthcare: Electrotherapy Pain & Rehabilitation Product Solutions from Rehabilicare. [Includes product description of SporTX and Ortho DX], http://www.mvp-design.com/sites/rehabilicare/all_products.htmi, (Aug. 2001), 3 pages.

Intelect Legend Stim Clinical Reference Manual, vol. 4 Intelect Legend Series, Chattanooga Group, Inc., (Jul. 2000) 25 pages.

Jette, D. U. et al.," Effect of Different Forms of Transcutaneous Electrical Nerve Stimulation on Experimental Pain," Physical Therapy, (Feb. 1986) vol. 66/No. 2, pp. 187–193.

Johnson, M. I. et al., "Analgesic Effects of Different Pulse Patterns of Transcutaneous Electrical Nerve Stimulation on Cold–Induced Pain in Normal Subjects," Journal of Psychosomatic Research (1991) vol. 35, No. 2/3, pp. 313–321, Great Britain.

Johnson, M. I. et al., "Analgesic Effects of Different Frequencies of Transcutaneous Electrical Nerve Stimulation on Cold–Induced Pain In Normal Subjects," Pain, (1989) 39, pp. 231–236, Elsevier Science Publishers B.V.

Johnson, M.I. et al., "An In–Depth Study of Long–Term Users of Transcutaneous Electrical Nerve Stimulation (TENS). Implications for Clinical Use of TENS," Pain (1991) 4, pp. 221–229, Elsevier Science Publishers B.V.

Katims, J.J. et al., "Transcutaneous Nerve Stimulation Frequency and Waveform Specificity in Humans," Appl. Neurophysiol. (1986) 49: pp. 86–91.

Landau, B. et al. "Neuromodulation Techniques for Medically Refractory Chronic Pain", Annu. Rev. Med. (Feb. 1993) 44: 279–87, Annual Reviews Inc.

Leem, J.W. et al., "Electrophysiological Evidence for the Antinociceptive Effect of Transcutaneous Electrical Stimulation on Mechanically Evoked Responsiveness of Dorsal Horms Neurons In Neuropathic Rats," Neuroscience Letters (1995) 192, pp. 197–200, Elsevier Science Ireland Ltd.

Lehmann T. et al. "Efficacy of Electroacupuncture and TENS In the Rehabilitation of Chronic Low Back Pain Patients", Pain (Sep. 1986) 26: 277–90, Elsevier Science Publishers B.V.

Liss, S. et al., "Physiological and Therapeutic Effects of High Frequency Electrical Pulses," Integrative Physiological and Behavioral Science, (Apr.–Jun. 1996) vol. 31, No. 2, pp. 88–94.

Marchand, S. et al., "Modulation of Heat Pain Perception by High Frequency Transcutaneous Electrical Nerve Stimulation (TENS)," The Clinical Journal of Pain (1991) 7: pp. 122–129, Raven Press Ltd., New York.

Model AWQ–104B Multi–Purpose Electronic Acupunctoscope Instruction Manual, 10 pages.

Moreno–Aranda, J. et al., "Electrical Parameters for Over–the–Skin Muscle Stimulation," J. Biomechanics, (1981) vol. 14, No. 9, pp. 579–585, Pergamon Press Ltd.

Moreno–Aranda, J. et al., "Investigation of Over–the–Skin Electrical Stimulation Parameters for Different Normal Muscles and Subjects," J. Biomechanics, (1981) vol. 14, No. 9, pp. 587–593, Pergamon Press Ltd., Great Britain.

O'Brien, W. J. et al., "Effect of Transcutaneous Electrical Nerve Stimulation on Human Blood B–Endorphin Levels," Physical Therapy, (Sep. 1984) vol. 64/No. 9, pp. 1367–1374.

Omura, Y., "Basic Electrical Parameters for Safe and Effective Electro Therapeutics [Electro–Acupuncture, TES, TENMS, (or TEMS), TENS and Electro Magnetic Field Stimulation with or without Drug Field] for Pain, Neuromuscular Skeletal Problems, and Circulatory Disturbances," Acupuncture & Electro Therapeutics Res., Int. J. (1987) vol. 12, pp. 201–225, Pergamon Journals Ltd., USA.

Omura, Y., Electrical Parameters for Safe and Effective Electro–Acupuncture and Transcutaneous Electrical Stimulation: Threshold Potentials for Tingling, Muscle Contraction and Pain: and How to Prevent Adverse Effects of Electro–Therapy, Acupuncture and Electro–Therapeutics Res., Int. J., (1985) vol. 10, Pergamon Press Ltd. USA.

Ordog, G.J., "Transcutaneous Electrical Nerve Stimulation versus Oral Analgesic: A Randomized Double–Blind Controlled Study in Acute Traumatic Pain," American Journal of Emergency Medicine, (Jan. 1987) vol. 5, No. 1, pp. 6–10.

Pointer F–3 Instruction Manual, ITO Co., Ltd., Tokyo, Japan (1999), 12 pages.

Radionics products brochure. "A Significant Breakthrough Using Pulsed Radiofrequency for Pain Management", Includes RF Lesion Generator System, Model RFG–3C Plus, (1997), Radionics. Burlington, MA, 10 pages.

Rehabilicare Ortho Dx product brochure. "Reduce Rehabilitation Time and Enhance Patient Comfort with Ortho Dx", Rehabilicare, New Brighton, MN, 2 pages.

Rehabilicare SMP–plus product brochure. "SMP–plus. The Pain Relief Solution for Hard to Treat Patients", Rehabilicare, New Brighton, MN (1999) 2 pages.

Rehabilicare SporTX Product Data Sheet, 1 page.

Rehabilicare SporTX Quick Set–Up Instructions, "SPORTX. Get back in the GAME!", Rehabilicare, New Brighton, MN, 2 pages.

Romita, V.V. et al., "Parametric Studies on Electroacupuncture–Like Stimulation in a Rat Model; Effects of Intensity, Frequency, and Duration of Stimulation on Evoked Antinociception," Brain Research Bulletin, (1997) vol. 42, No. 4, pp. 289–299, Elsevier Science Inc., USA.

Rooney, J.G. et al., "Effect of Variation in the Burst and Carrier Frequency Modes of Neuromuscular Electrical Stimulation on Pain Perception of Healthy Subjects," Physical Therapy, (Nov. 1992) vol. 72, No. 11, pp. 800–809.

Sluka, K.A. et al., "Treatment with either High or Low Frequency TENS Reduces the Secondary Hyperalgesia Observed After Injection of Kaolin and Carrageenan into the Knee Joint," Pain, (1998) 77, pp. 97–102, Elsevier Science B.V.

Somers, D.L., et al., "High–Frequency Transcutaneous Electrical Nerve Stimulation Alters Thermal but not Mechanical Allodynia Following Chronic Constriction Injury of the Rat Sciatic Nerve," Arch. Phys. Med. Rehabil., (1998) 79, pp. 1370–1376.

Starobinets, M. et al., "Analgesic Effect of High–Frequency and Acupuncture Like Transcutaneous Electric Stimulation of Nerve Fibers in Spinal Osteochondrosis," (Russian) Zhurnal Nevropatologii I Psikhiatrii Imeni S.S. Korsakova (1985) 85, (3), pp. 350–354.

Ulett, G. et al. "Electroacupuncture: Mechanisms and Clinical Application", Biological Psychiatry (Jul. 1998) 44: 129–38.

Van Doren, C.L., "Contours of Equal Perceived Amplitude and Equal Perceived Frequency for Electrocutaneous Stimuli," Perception and Psychophysics (1997) 59, (4), pp. 613–622.

White, P. et al. "Percutaneous Neuromodulation Therapy: Does the Location of Electrical Stimulation Effect the Acute Analgesic Response?", Anesthesia & Analgesia (Oct. 2000) 91: 1–6.

White, P. et al. "The Effect of Montage on the Analgesic Response to Percutaneous Neuromodulation.Therapy" Anesthesia & Analgesia (Feb. 2001) 92: 483–7.

PCT International Search Report for International Application No. PCT/US01/31441; mailed May 7, 2002; Applicant: Vertis Neuroscience, Inc., 8 pages.

PCT International Search Report for International Application No. PCT/US02/25551; mailed Feb. 18, 2003; Applicant: Vertis Neuroscience, Inc. 8 pgs.

U.S. Appl. No. 09/667,183, Leonard, filed Sep. 21, 2000.

U.S. Appl. No. 09/686,993, Gliner, filed Oct. 10, 2000.

U.S. Appl. No. 09/751,503, Gliner, filed Dec. 12, 2000.

U.S. Appl. No. 29/130,210, Leonard et al., filed Sep. 28, 2000.

U.S. Appl. No. 29/134,817, Bishay et al., filed Dec. 29, 2000.

* cited by examiner

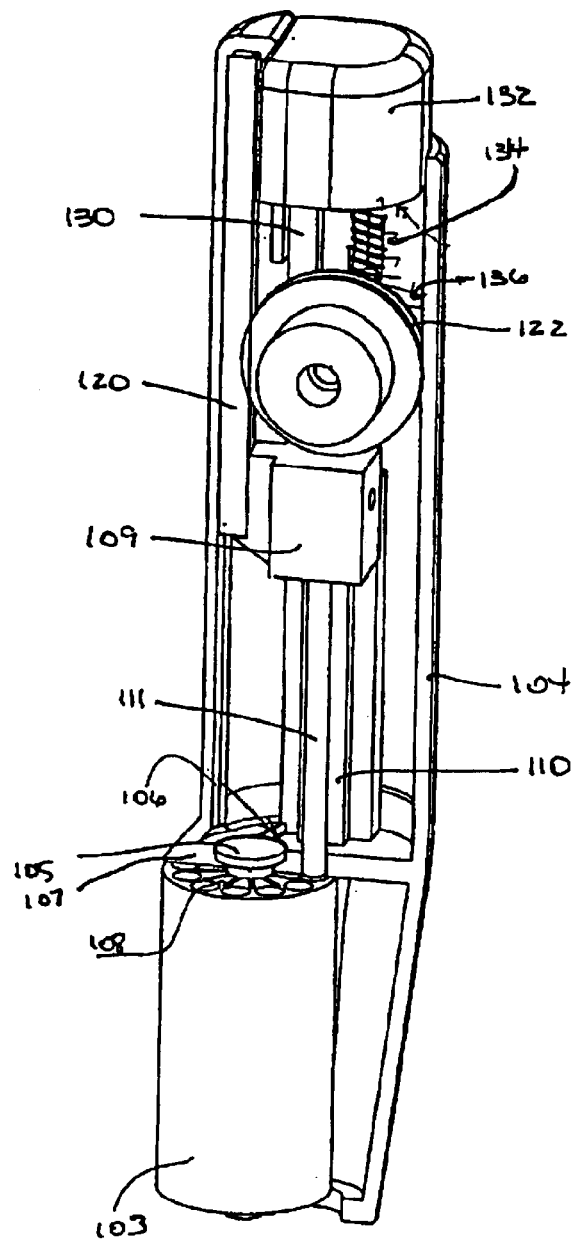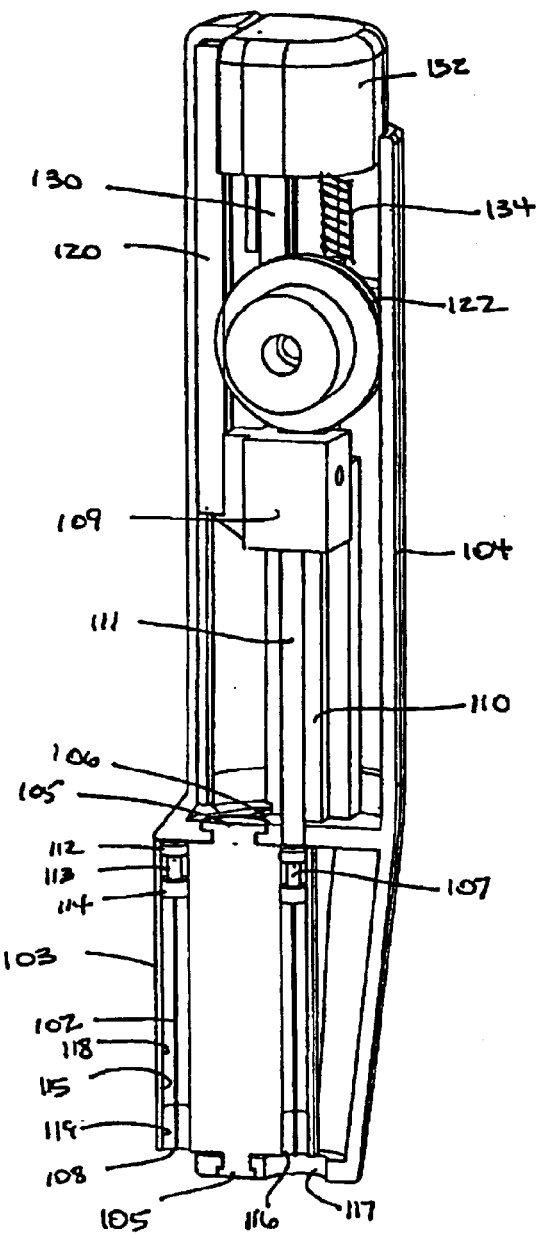
Fig. 14
Fig. 15

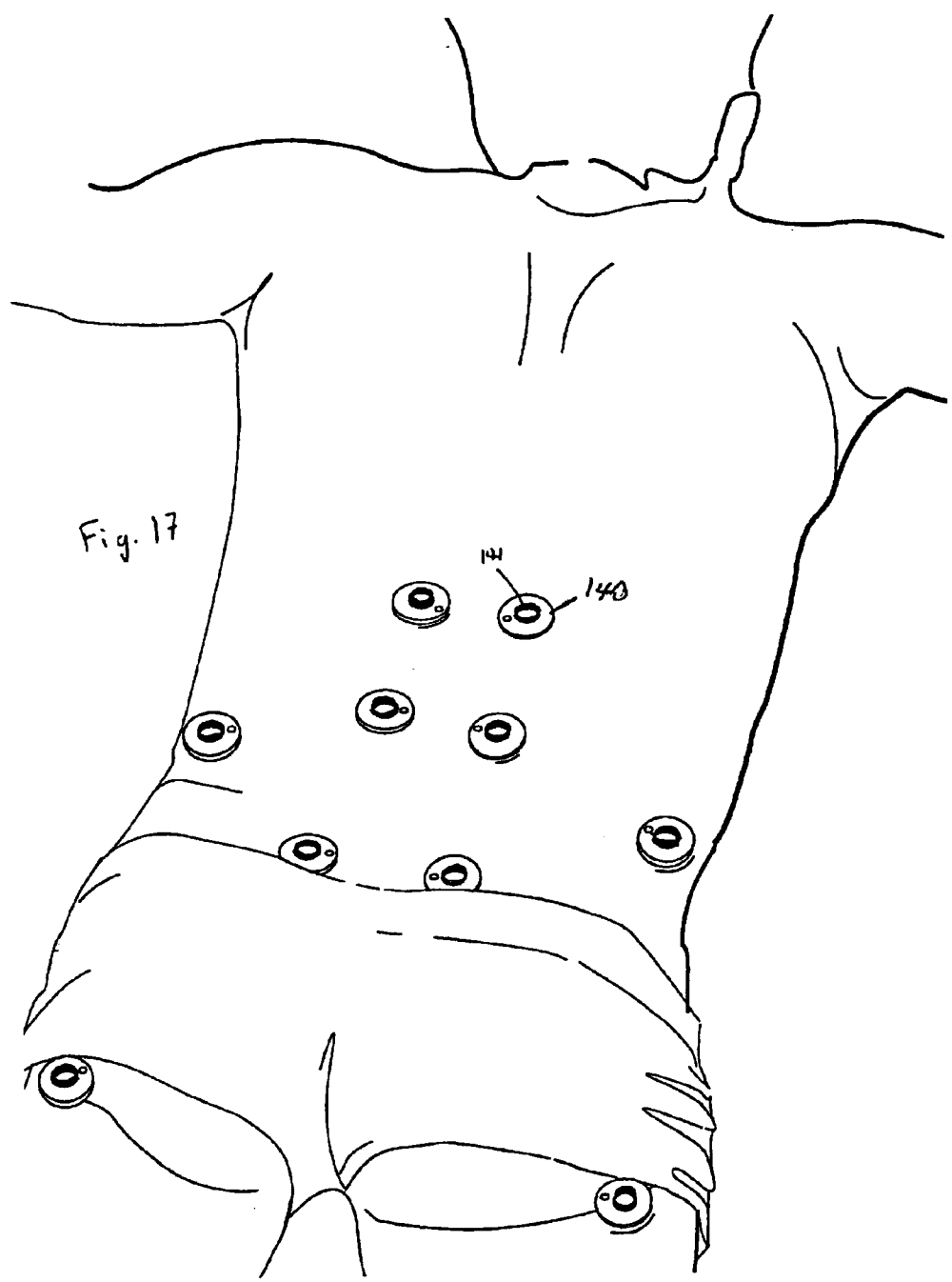

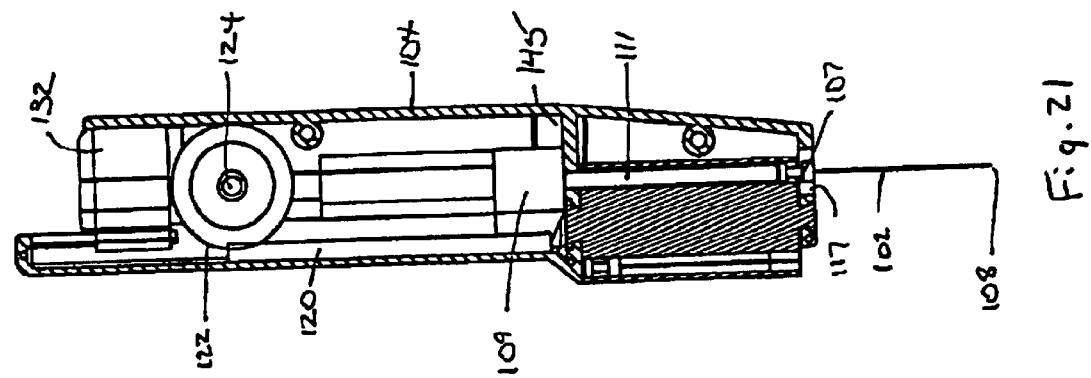

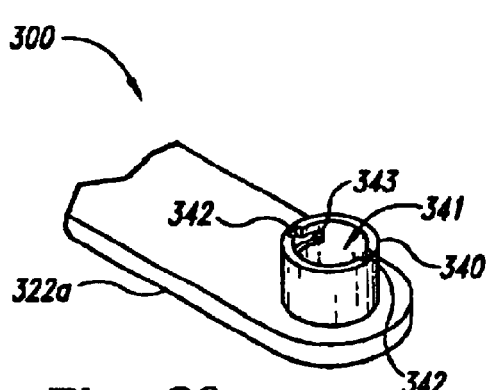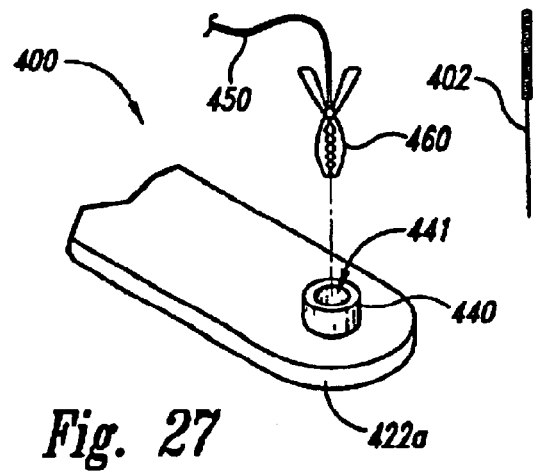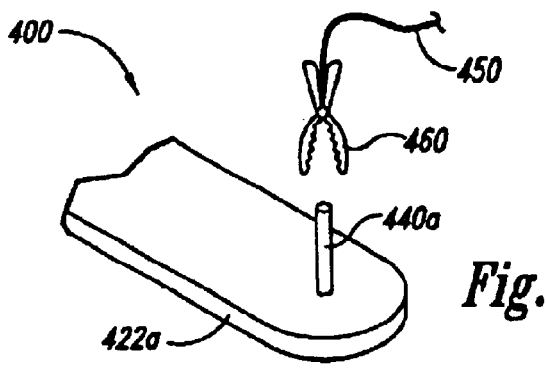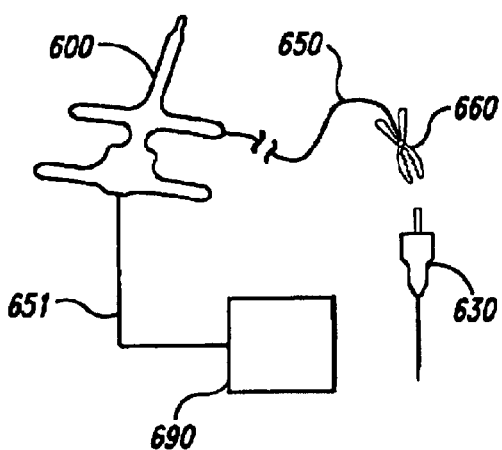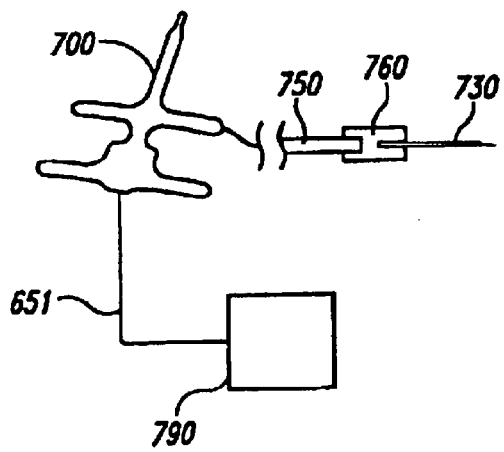

APPARATUS AND METHOD FOR COUPLING THERAPEUTIC AND/OR MONITORING EQUIPMENT TO A PATIENT

CROSS-REFERENCE TO RELATED APPLICATIONS

This application is a continuation-in-part of: (1) U.S. application Ser. No. 09/452,477, titled "Percutaneous Electrical Therapy System with Electrode Entry Angle Control," filed Dec. 1, 1999; now U.S. Pat. No. 6,622,051 and (2) U.S. application Ser. No. 09/666,931, titled "Method and Apparatus for Repositioning a Percutaneous Probe," filed Sep. 21, 2000 now U.S. Pat. No. 6,529,776, both incorporated herein in their entireties by reference.

TECHNICAL FIELD

This invention relates generally to apparatuses and methods for coupling therapeutic and/or monitoring equipment to a patient.

BACKGROUND

Electrical therapy has long been used in medicine to treat pain and other conditions. For example, transcutaneous electrical nerve stimulation (TENS) systems deliver electrical energy through electrode patches placed on the surface of a patient's skin to treat pam in tissue beneath and around the location of the patches. However, the TENS systems may not adequately alleviate pain in certain circumstances.

More recently, a technique in which electrodes are placed through the patient's skin into the target tissue has been proposed. Percutaneous Neuromodulation Therapy ("PNT") (also sometimes called Percutaneous Electrical Nerve Stimulation or "PENS") using percutaneously placed electrodes achieves significantly better pain relief results than TENS treatments using skin surface electrodes. This therapy is described in Ghoname et al., "Percutaneous Electrical Nerve Stimulation for Low Back Pain," JAMA 281:818–23 (1999); Ghoname et al., "The Effect of Stimulus Frequency on the Analgesic Response to Percutaneous Electrical Nerve Stimulation in Patients with Chronic Low Back Pain," Anesth. Analg. 88:841–6 (1999); Ahmed et al., "Percutaneous Electrical Nerve Stimulation (PENS): A Complementary Therapy for the Management of Pain Secondary to Bony Metastasis," Clinical Journal of Pain 14:320–3 (1998); and Ahmed et al., "Percutaneous Electrical Nerve Stimulation: An Alternative to Antiviral Drugs for Herpes Zoster," Anesth. Analg. 87:911–4 (1998). The contents of these references are incorporated herein by reference.

Thus far, PNT practitioners have used percutaneously placed acupuncture needles attached to waveform generators via cables and alligator clips to deliver the therapy to the patient. One feature of conventional PNT systems is that they typically include a number of electrical cables that must be properly connected to the corresponding percutaneous electrodes to deliver effective electrical therapy. Accordingly, a drawback with these conventional systems is that it can be difficult (particularly for inexperienced practitioners) to connect each electrical cable to the proper corresponding electrode. This drawback is shared as well by other systems that require multiple connections to the patient. Such systems include electrical monitoring systems and drug delivery systems.

SUMMARY

The invention is directed to apparatuses and methods for supporting therapeutic and/or diagnostic couplers for removable coupling to a recipient. An apparatus in accordance with one aspect of the invention can include a support member configured to rest on a body of the recipient proximate to a coupling region. The support member can include a first coupler location configured to removably carry a first coupler proximate to a first coupling position of the body of the recipient. The support member can further include a second coupler location configured to removably carry a second coupler proximate to a second coupling position of the body of the recipient. In one aspect of the invention, the support member can be spaced apart from the first and second coupling positions. In another aspect of the invention, the support member can be elongated along a support member axis and the first coupler location can be positioned closer than the second coupler location to the support member axis. In still another aspect of the invention, the first coupler location can be positioned closer than the second coupler location to the first coupling position. Accordingly, the apparatus can guide a practitioner to connect the couplers to the correct coupling position.

In another aspect of the invention, the support member can be flexible and resilient to conform to a surface of the body, and can be shaped to rest on at least one of a back, a neck, a head, and a leg of the recipient. The apparatus can further include a flexible link coupled between the first coupler and the support member. The link can remain connected between the first coupler and the support member when the first coupler is moved from an attached position to a detached position and then to a coupled position with the coupler coupled to the body of the recipient. The link can include an electrical cable configured to be coupled to a source of electrical pulses, an electrical cable configured to be coupled to a signal monitor, and/or a length of tubing configured to be coupled to a source of liquid medicament.

In yet another aspect of the invention, the first and second coupling positions can be two of a larger plurality of coupling positions and the first and second coupler locations can be two of a larger plurality of coupler locations. An outline of the coupling positions can define a first shape and an outline of the coupler locations can define a corresponding second shape at least generally similar to the first shape.

The invention is also directed toward a method for coupling therapy and/or monitoring equipment to a recipient. The method can include positioning a support member against a body of a recipient proximate to a coupling area, supporting a first coupler relative to the body at a first coupler location of the support member proximate to a first coupling position of the body, and supporting a second coupler relative to the body at a second coupler location of the support member proximate to a second coupling position of the body. In one aspect of the invention, the support member can be elongated along a support member axis and the first coupler location can be positioned closer than the second coupler location to the first coupling position and/or to the support member axis. In another aspect of the invention, the support member can be spaced apart from the first and second coupling positions. The method can further include removing the first coupler from the support member and coupling the first coupler to the body at the first coupling position, and removing the second coupler from the support member and coupling the second coupler to the body at the second coupling position.

BRIEF DESCRIPTION OF THE DRAWINGS

FIG. 1A shows electrode and angle of insertion assemblies wherein the electrode is in an undeployed and uninserted state.

FIG. 1B shows the electrode and angle of insertion assemblies of FIG. 1A during deployment but prior to insertion of the electrode into a patient's tissue.

FIG. 1C shows the electrode and angle of insertion assemblies of FIG. 1A during deployment and insertion of the electrode into the patient's tissue.

FIG. 1D shows the electrode of FIG. 1A inserted into the patient's tissue.

FIG. 1E shows the electrode of FIG. 1A attached to a control unit to provide percutaneous electrical therapy.

FIG. 1F shows the electrode and angle of insertion assemblies of FIG. 1A during undeployment but prior to removing the electrode from the patient's tissue.

FIG. 1G shows the electrode and sharp point protection assemblies of FIG. 1A during undeployment and after removing the electrode from the patient's tissue.

FIG. 2A shows a percutaneous electrical therapy system with electrode and angle of insertion assemblies wherein the electrode is in an undeployed and uninserted state.

FIG. 2B shows the percutaneous electrical therapy system of FIG. 2A during deployment, but prior to insertion, of the electrode.

FIG. 2C shows the percutaneous electrical therapy system of FIG. 2A with the electrode in a deployed and inserted state.

FIG. 2D shows the percutaneous electrical therapy system of FIG. 2A during undeployment of the electrode.

FIG. 2E shows the percutaneous electrical therapy system of FIG. 2A after the electrode has been undeployed.

FIG. 14 is a partial sectional view of the introducer and angle of insertion assembly of FIG. 13.

FIG. 15 is a sectional view of the introducer and angle of insertion assembly of FIG. 13.

FIG. 17 shows part of the electrode assembly of the embodiment of FIGS. 13–16 in a montage used for treating low back pain using PNT.

FIG. 19 is a sectional view showing the introducer of FIG. 13 in the process of deploying an electrode, prior to insertion of the electrode.

FIG. 20 is a sectional view showing the introducer of FIG. 13 in the process of deploying an electrode, during insertion of the electrode.

FIG. 21 is a sectional view showing the introducer of FIG. 13 in the process of deploying an electrode, also during insertion of the electrode.

FIG. 26 is a top isometric view of a portion of a coupler support configured to support a coupler in accordance with another embodiment of the invention.

FIG. 27 is a top isometric view of a portion of a coupler support having an aperture configured to receive a clamp-type coupler in accordance with still another embodiment of the invention.

FIG. 28 is a top isometric view of a portion of a coupler support having a post configured to be clamped by a clamp-type coupler in accordance with yet another embodiment of the invention.

FIG. 29 is a partially schematic illustration of an arrangement that includes a coupler support configured to support couplers for receiving diagnostic information in accordance with yet another embodiment of the invention.

FIG. 30 is a partially schematic illustration of an arrangement that includes a coupler support configured to support a plurality of couplers that administer liquid medicament in accordance with still another embodiment of the invention.

DETAILED DESCRIPTION

Percutaneous electrical therapy systems, such as PNT systems, deliver electric current to a region of a patient's tissue through electrodes that pierce the skin covering the tissue. The electric current is generated by a control unit external to the patient and typically has particular waveform characteristics such as frequency, amplitude and pulse width. Depending on the treatment or therapy being delivered, there may be one electrode containing both a cathode and an anode or a plurality of electrodes with at least one serving as a cathode and at least one serving as an anode.

The electrode has a sharp point not only to facilitate insertion through the patient's skin but also to enhance local current density during treatment. The placement and location of the electrode point is therefore an important aspect of the therapy. The electrodes must also be properly coupled to the control unit to form a complete circuit for delivering therapeutic electric current to the patient.

Figure 1A:
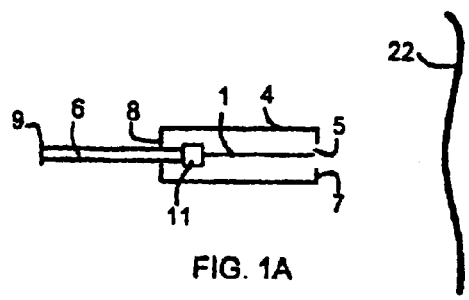
FIGS. 1A–G are schematic renderings of a percutaneous electrical therapy system according to one embodiment of this invention.
Figure 1B:
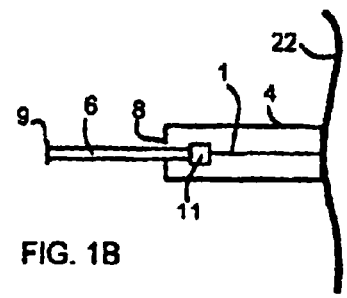

FIGS. 1A–G are block diagrams showing deployment and use of a percutaneous electrical therapy system and electrode assembly in accordance with an embodiment of the invention. As shown in FIGS. 1A and 1B, the system can include an electrode 1 having a sharp point 2 at its distal end and a housing 4 surrounding at least the sharp point 2 when the electrode 1 is in its undeployed and uninserted states. The undeployed and uninserted states include pre-deployment and post-deployment states of the electrode 1. The housing 4 can have an aperture 5 at its distal end. An actuator 6 can interact with a handle 11 at the proximal end of electrode 1 as shown to move the electrode 1.

Figure 1C:
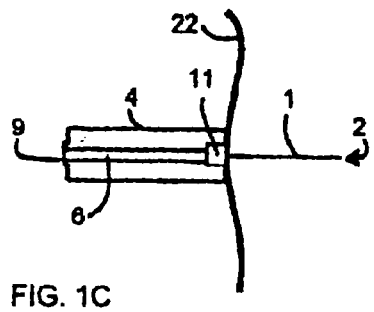

Deployment of the electrode assembly can include the steps taken to place the electrode assembly in proper position and condition for use in electrical therapy. FIG. 1A shows the electrode assembly in an undeployed (pre-deployed) state. During deployment, the distal face 7 of housing 4 is placed against a patient's skin 22, as shown in FIG. 1B. This action supports housing 4 with respect to the patient's skin, thereby controlling the angle between the housing and the patient's skin. Electrode 1 is then inserted through aperture 5 into the tissue underlying the patient's skin by moving actuator 6 distally, as shown in FIG. 1C. As it moves, actuator 6 (and therefore electrode 1) is supported by housing 4 to control the angle at which the electrode 1 enters into the patient's tissue.

The actuator 6 may have a limit stop 9 element cooperating with a limit stop area 8 of the housing 4 to limit distal motion of the actuator 6 and to control the depth of insertion of the sharp point 2 of the electrode 1. In one embodiment, for example, when the electrical therapy system is used to provide percutaneous neuromodulation therapy, the predetermined electrode depth is 3 cm. Other electrode depths may be used, of course, depending on the intended application and therapy.

Figure 1D:
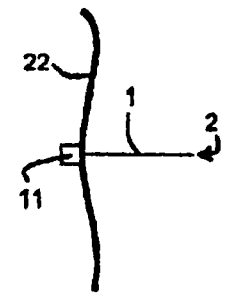
Figure 1E:
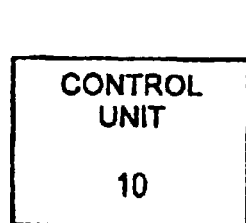
Figure 1F:
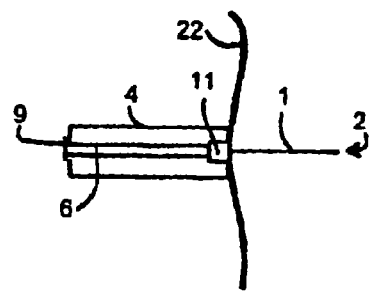

After insertion, the housing 4 and the actuator 6 (which have heretofore acted as an electrode introducer) can be removed, as shown in FIG. 1D. The electrode 1 can be connected to a control unit 10 via a conductor or cable 16. For use with PNT, the control unit 10 can supply a current-regulated and current-balanced waveform with an amplitude of up to approximately 20 mA, a frequency between approximately 4 Hz and 50 Hz, and pulse width of between approximately 50 $\mu$sec and 1 msec. Other electrical waveforms having other parameters may be used, of course, depending on the therapy to be provided. Also, while FIG. 1E shows only one electrode connected to the control unit, it should be understood that a plurality of electrodes may be connected to a single control unit.

Figure 1G:
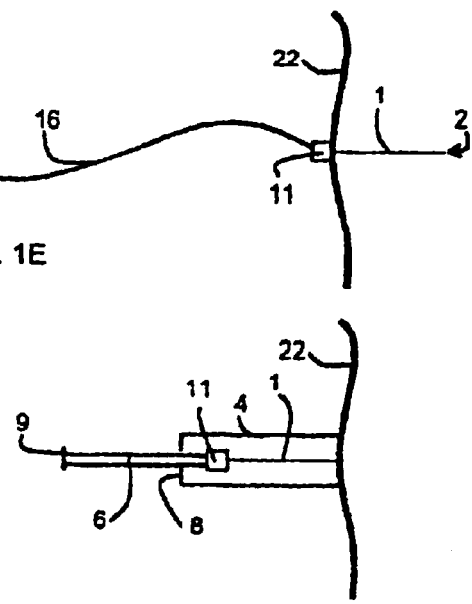

After completion of the electrical therapy, the electrode assembly can be undeployed. In an embodiment shown in FIG. 1F, the aperture 5 of housing 4 is placed over the handle portion 11 of electrode 1. Housing 4 may be the same housing used to deploy and insert the electrode (i.e., the electrode introducer), or it may be an entirely different assembly (e.g., an electrode remover). The sharp point 2 of electrode 1 is then drawn into housing 4 of sharp point protection assembly 3 by moving actuator 6 proximally, as shown in FIG. 1G.

FIGS. 2A–E are block diagrams showing another embodiment of the invention. In one aspect of this embodiment, a control unit 10 is connected to an electrode 12 within an electrode assembly 13 via a conductor 16. As above, for use with PNT, the control unit 10 can supply a current-regulated and current-balanced waveform with an amplitude of up to approximately 20 mA, a frequency between approximately 4 Hz and 50 Hz, and pulse width of between approximately 50 $\mu$sec and 1 msec. In other embodiments, the control unit 10 can supply electrical current having other characteristics. As shown in its undeployed state in FIG. 2A and in its uninserted stated in FIG. 2B, the system can include a housing 18 surrounding the sharp point 20 of electrode 12 when the electrode point 20 has not yet been inserted through the patient's skin 22.

Figure 2A:
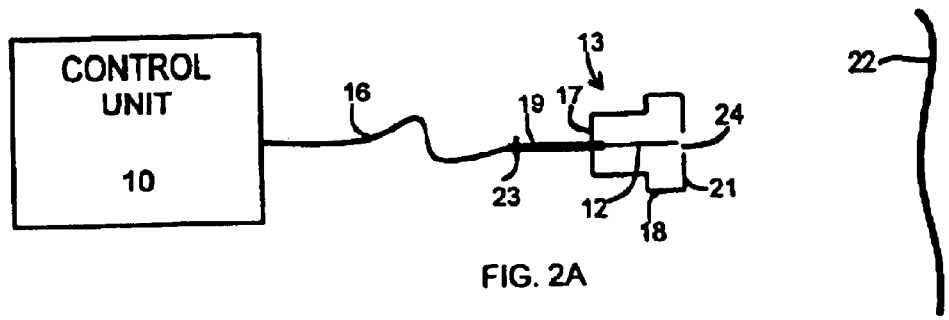
FIGS. 2A–E are schematic renderings of a percutaneous electrical therapy system according to another embodiment of this invention.
Figure 2B:
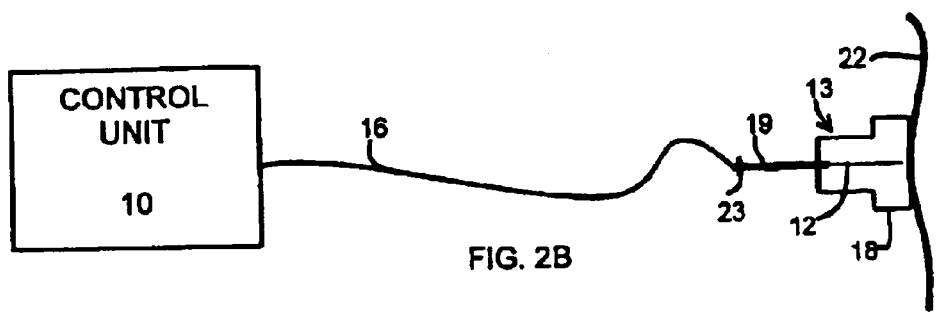
Figure 2C:
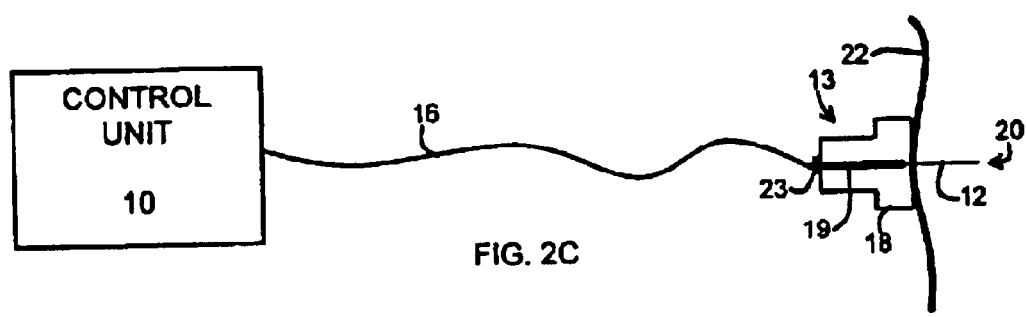

To begin deployment, a distal face 21 of the housing 18 is placed against the patient's skin 22, as shown in FIG. 2B. As with the previous embodiment, this action supports the housing 18 with respect to the patient's skin, thereby controlling the angle between the housing and the patient's skin. The sharp point 20 of electrode 12 is then inserted through an aperture 24 into the tissue underlying the patient's skin by moving an actuator 19 distally, as shown in FIG. 2C. As it moves, the actuator 19 (and therefore the electrode 12) is supported by the housing 18 to control the angle at which the electrode enters into the patient's tissue.

The actuator 19 may be part of the electrode assembly 13 or a separate component of the system. The actuator 19 may also have a limit stop element 23 that cooperates with a limit stop area 17 of housing 18 to limit distal movement of actuator 19, thereby controlling the depth of insertion of electrode 12. In one embodiment, for example, when the electrical stimulation system is used to provide percutaneous neuromodulation therapy, the predetermined electrode depth is approximately 3 cm, although other electrode depths may be used depending on the application. The control unit 10 may then provide the appropriate therapy to the patient through the electrode 12 and any other electrodes connected to it.

Figure 2D:
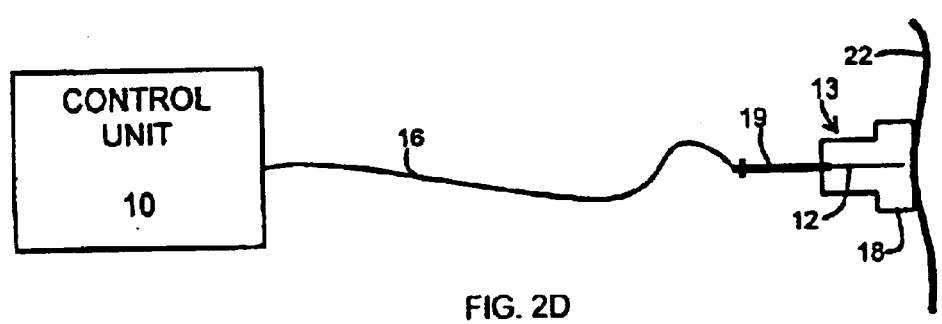
Figure 2E:
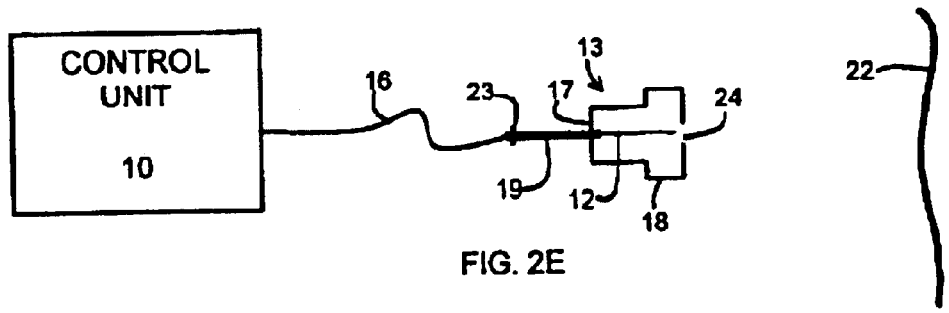

During undeployment, the actuator 19 can draw the electrode 12 back proximally into the housing 18. After the electrode 12 is removed from the patient's skin, the housing 18 of sharp point protection assembly 14 once again surrounds the sharp point 20 of the now uninserted electrode 12, as shown in FIGS. 2D and 2E. The actuator 19 helps enable this operation to occur without ever exposing the sharp point 20 of the electrode 12 when the sharp point 20 is no longer in the patient. In fact, the operator of the electrode assembly never sees the sharp point 20 of the electrode 12. Thus, sharp point protection assembly 14 shields the potentially contaminated portion of the undeployed electrode 12 and protects the patient's caregiver or other bystander from unintended contact with the sharp point 20 of the electrode 12 before, during and after electrical therapy.

While FIGS. 2A–E show the electrode connected to the control unit prior to deployment and insertion of the electrode into the patient's skin, the connection between the control unit and the electrode could be made during deployment or after insertion. Also, while FIGS. 2A–E show only one electrode connected to the control unit, it should be understood that a plurality of electrodes may be connected to a single control unit, as called for by the desired electrical stimulation treatment.

Figure 3:
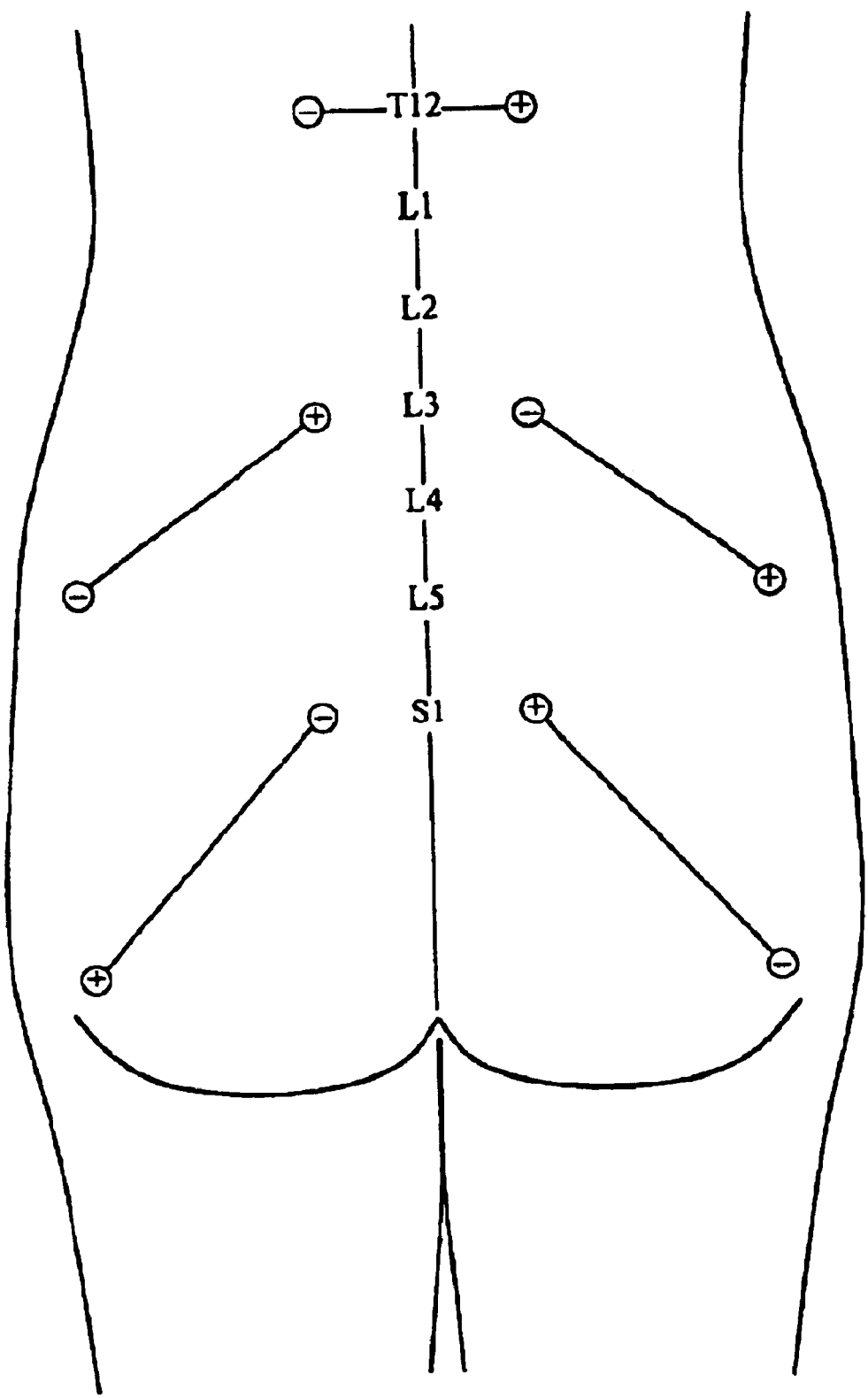
FIG. 3 shows an electrode montage for use in percutaneous neuromodulation therapy to treat low back pain.
Figure 4:
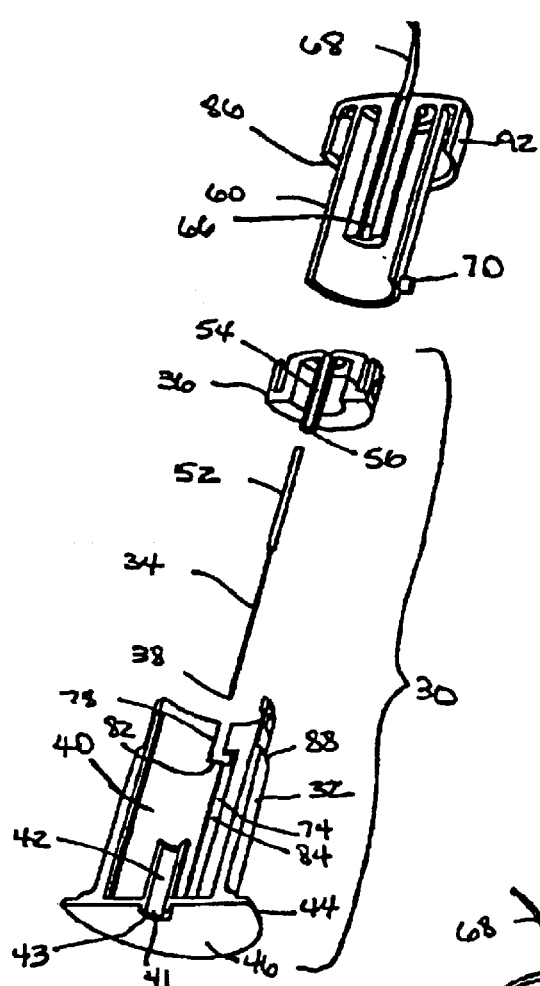
FIG. 4 is an exploded sectional view of an electrode and angle of insertion assembly according to yet another embodiment of this invention.
Figure 5:
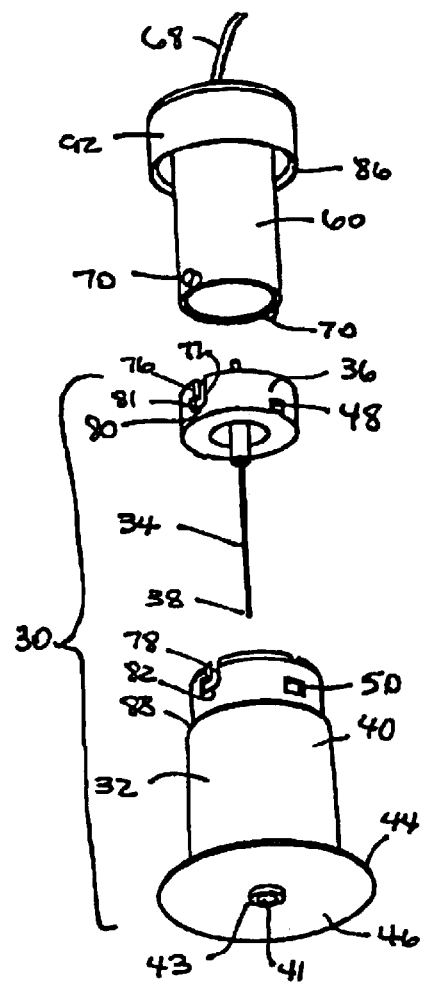
FIG. 5 is a partially exploded elevational view of the embodiment of FIG. 4.
Figure 6:
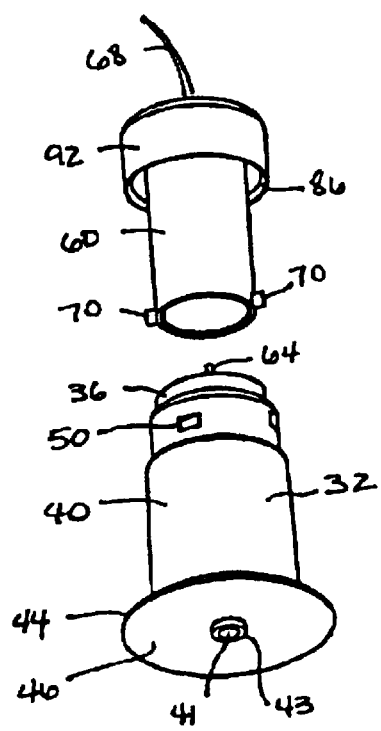
FIG. 6 is an elevational view of the embodiment of FIG. 4 showing the electrode and angle of insertion assemblies and a coupler.
Figure 7:
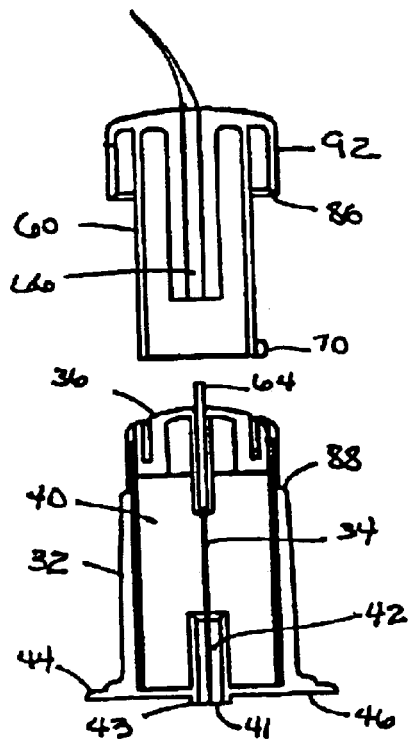
FIG. 7 is a sectional view of the embodiment of FIG. 4 showing the electrode and angle of insertion assemblies and a coupler.
Figure 8:
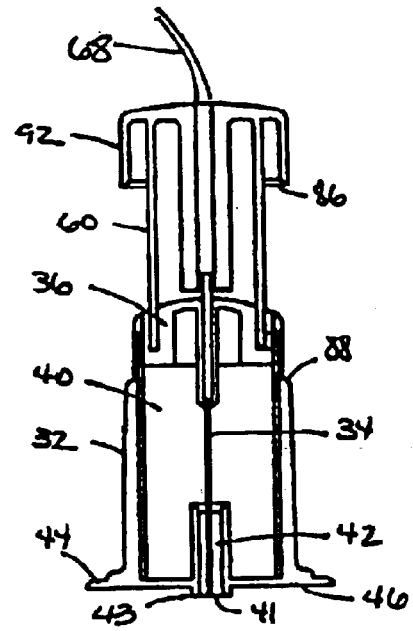
FIG. 8 is a sectional view of the embodiment of FIG. 4 showing the coupler in engagement with the electrode and angle of insertion assemblies prior to insertion of the electrode into a patient's tissue.
Figure 9:
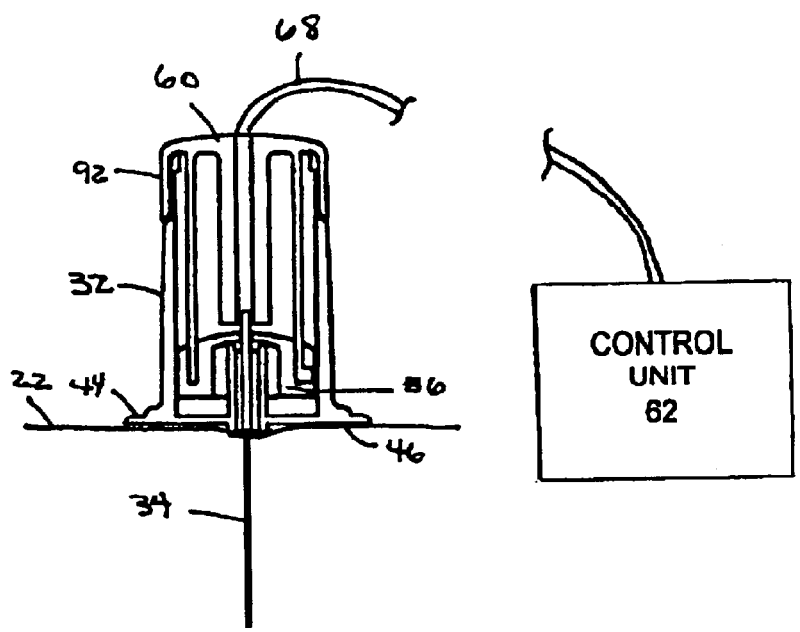
FIG. 9 is a sectional view of the embodiment of FIG. 4 with the electrode in its deployed and inserted state.

To use the percutaneous electrical therapy systems of FIGS. 1A–G and FIGS. 2A–E to treat a patient, one or more electrodes are inserted through the patient's skin into the underlying tissue. As an example, to treat low back pain using PNT with unipolar electrodes, an array or montage such as that shown in FIG. 3 may be used. The "T12"-"S1" designations refer to the patient's vertebrae. The control unit or generator supplies current pulses between pairs of electrodes for durations of a few minutes to several hours, preferably delivering the current-regulated waveform described above. Thirty-minute treatments are recommended in the Ghoname et al. low back pain treatment articles.

FIGS. 4–12 show a system in accordance with another embodiment of this invention. An electrode assembly 30 can include a base 32, an electrode 34, and a plunger or actuator 36. The base 32 can have a flange or flared end 44 that is adapted to make contact with a patient's skin. The base 32 may be formed from any suitable polymer or metal, such as a high-density polyethylene (HDPE). The base 32 can be opaque so that the electrode 34 cannot be seen by a needle-shy patient.

The actuator 36 fits within a housing portion 40 of base 32 in a slidable arrangement. A locking assembly can prevent relative movement between the actuator 36 and the housing 40 of the base 32. In one embodiment, the locking assembly of the actuator 36 has integrally-formed resilient detents 48 on its exterior cylindrical surface. In the undeployed state of electrode assembly 30, the detents 48 mate with corresponding openings 50 in the base 32 to hold the actuator 36 and the base 32 in place with respect to each other to prevent the electrode 34 from moving outside of the protective housing 40 of the base 32, thereby providing sharp point protection. In other embodiments, mechanisms other than the detent and opening arrangement may be used to hold the actuator and base in place.

In one embodiment, the electrode 34 can include a 3-cm long 32-gauge stainless steel needle. Other sizes and materials may be used for the electrode 34, of course, without departing from the scope of the invention. The actuator 36 can be formed from HDPE as well, although other suitable materials may be used.

The electrode 34 can have a larger-diameter handle 52 at its proximal end. The handle 52 can fit within a channel 54 formed within the actuator 36. The channel 54 can have a narrow opening 56 at its distal end, with a diameter slightly larger than the diameter of electrode 34 but narrower than the diameter of handle 52 to hold electrode 34 in place within the actuator 36 after initial manufacture and assembly. In the undeployed state shown in FIG. 7, the sharp point 38 of electrode 34 is disposed within housing portion 40 of base 32, specifically, within a narrow channel 42 of the housing 40.

To deploy one or more electrode assemblies on a patient in order to provide electrical stimulation therapy (such as PNT), the distal surface 46 of the flange portion 44 of the base 32 can be mounted on the desired site on the patient's skin, preferably with a compressible adhesive pad (not shown) surrounding a ring 43 extending downward from surface 46 around an aperture 41 formed at the distal end of channel 42, although other means of attaching base 32 to the patient may be used as appropriate. This action aligns the base 32 with respect to the patient's skin. The flange portion 44 of the base 32 provides extra stability for the electrode assembly during electrode insertion and use.

A coupler or actuator tool 60 can be used to both insert the electrode and connect the electrode electrically with a control unit 62. The coupler 60 and the electrode assembly 30 can also interact to provide the sharp point protection assembly of this embodiment. When the distal end of the coupler 60 is placed against the proximal ends of the base 32 and the actuator 36, the exposed proximal end 64 of the electrode handle 52 makes electrical contact with a contact surface 66 within the coupler 60. The contact surface 66, in turn, can be electrically connected to the control unit 62 via a cable or other conductor 68.

The coupler 60 can have two oppositely disposed pegs 70 extending outwardly from the distal portion of its cylindrically surface. The pegs 70 can mate with two corresponding slots 72 in the actuator 36 and with two corresponding grooves 74 in the base 32. The second of the two slots 72 and the second of the two grooves 74 are each opposite the slot 72 and groove 74, respectively, shown in FIGS. 4 and 5. When connecting the coupler 60 to the electrode assembly 30, the pegs 70 move along longitudinal portions 76 of the slots 72 and along longitudinal portions 78 of the grooves 74. Concurrently, the exposed distal end 64 of the electrode handle 52 begins to make sliding contact with the contact surface 66 of actuator tool 60 to create the electrical connection between coupler 60 and the electrode 32.

The coupler 60 can be rotated clockwise (looking down on the assembly), after the pegs 70 reach the end of the longitudinal portions 76 and 78. Accordingly, the pegs 70 move into short circumferential portions 80 and 82, respectively, of the slots 72 and the grooves 74. The length of the circumferential portions 80 of the slots 72 is less than the length of the circumferential portions 82 of the grooves 74. Continued movement of the pegs 70 along the circumferential portions 82 will therefore move the pegs 70 against the ends 81 of the circumferential slots 80. Further clockwise rotation of the coupler 60 will cause the actuator 36 to rotate clockwise as well, thereby moving the detents 48 out of the openings 50 and allowing the electrode 34 and the actuator 36 to move with respect to base 32.

Second longitudinal portions 84 of the grooves 74 can be formed in base 32 at the end of circumferential portions 82. Movement of the pegs 70 distally along the second longitudinal portions 84 pushes the pegs 70 against the distal edges of the circumferential slot portions 80, thereby moving the actuator 36 and the electrode 34 in a controlled fashion distally toward the patient's skin 22.

As it moves, the electrode 34 passes through the channel 42, and the sharp point of electrode 34 moves out through aperture 41. The channel 42 and the actuator 36 provide axial support to the electrode 34 during this forward movement and also, along with the support provided by the flange 44, provide entry angle guidance to the electrode 34. In addition, downward pressure on the patient's skin during electrode deployment can compress the compressible adhesive pad and press the ring 43 against the patient's skin 22, which helps ease electrode entry through the skin and also lessens the insertion pain experienced by the patient.

The alignment of the base 32 with respect to the patient's skin and the controlled movement of the actuator 36 and the electrode 34 within the base 32 can control the angle at which the electrode enters the tissue underlying the patient's skin. Distal movement of the electrode 34 and its actuator within the base 32 can continue until a distal surface 86 of a cylindrical cap portion 92 of the coupler 60 meets an annular surface 88 of housing 40. At this point, the sharp point 38 of the electrode 34 has extended a predetermined depth into the tissue underlying the patient's skin. In one embodiment, this predetermined depth is approximately 3 cm, and the depth can have other values depending on the treatment to be performed.

The electrode assembly 30 can also include a deployed electrode holding mechanism. In one aspect of this embodiment, an interference fit between the inner surface of channel 42 and the outer surface 55 of channel 52 performs this function.

Electrical stimulation treatment may begin once the electrodes have been deployed and inserted. The control unit 62 can supply stimulation current to the electrodes, e.g., in the manner described in the Ghoname et al articles. The electrical waveform provided by the control unit depends on the application. For example, in one embodiment, the control unit 62 can provide a current-regulated and current-balanced waveform with an amplitude of up to approximately 20 mA, frequency between approximately 4 Hz and 50 Hz, and pulse width of between approximately 50 $\mu$sec and 1 msec. In other embodiments, the control unit 62 can provide electrical current at other frequencies.

The interaction of the coupler 60 and the base 32 can provide stability to the electrode 34 and its electrical connection to the control unit during treatment by holding the electrode in place, by providing strain relief for tugging forces on the cable 68, and by providing a robust mechanical connection. It should also be noted that in one aspect of these embodiments, the sharp point of the electrode 34 is not exposed to the operator or to any other bystander at any point during deployment and use of the electrode assembly.

After treatment has been completed, the electrode may be removed from the patient. To do so, the coupler 60 can be moved proximally away from the patient. As the pegs 70 move proximally along the longitudinal portions 84 of the grooves 74, the pegs 70 push against the proximal edges of the actuator's circumferential slot portions 80, thereby moving the actuator 36 and the electrode 34 proximally as well. When the pegs 70 reach the proximal end of the longitudinal groove portions 84, the sharp end 38 of the electrode 34 is out of the patient and safely inside the housing 40 of the base 32. Counterclockwise movement of the coupler 60 moves the pegs 70 along the circumferential portions 80 and 82 of the slot 72 and the groove 74, respectively. Because the circumferential portion 80 is shorter than the circumferential portion 82, this counterclockwise movement will turn the actuator 36 counterclockwise.

At the limit of the counterclockwise movement, the detents 48 move back into the openings 50 to prevent further movement of the electrode and the actuator with respect to the base 32. Further distal movement of the coupler 60 moves the pegs 70 distally along the longitudinal portions 76 and 78 of the slot 72 and the groove 74, respectively, to disconnect the coupler 60 from the electrode assembly 30. The base 32 can then be removed from the patient.

Figure 10:
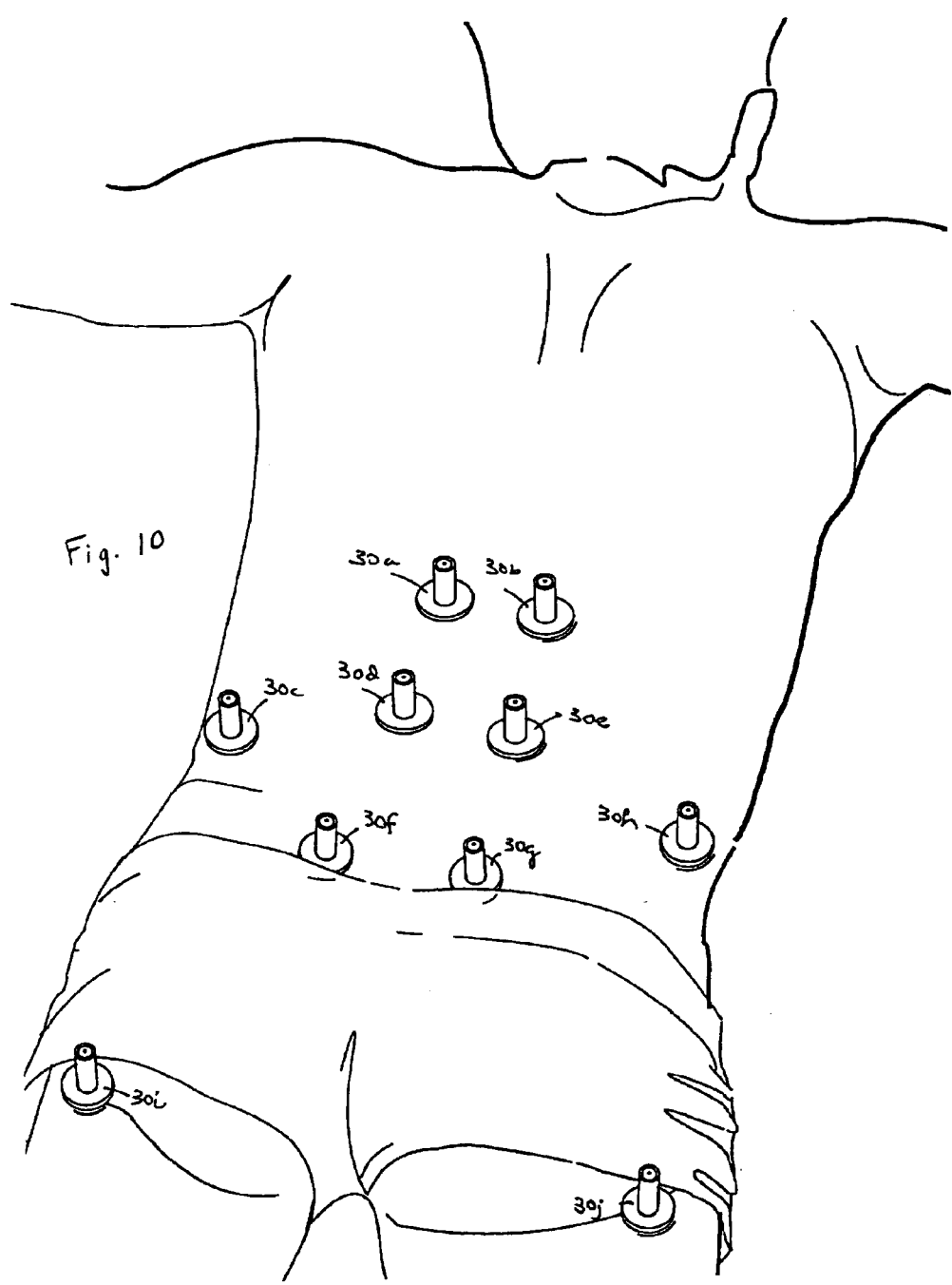
FIG. 10 shows a montage for using the embodiment of FIG. 4 to treat low back pain with the electrodes in a partially deployed but uninserted state.
Figure 11:
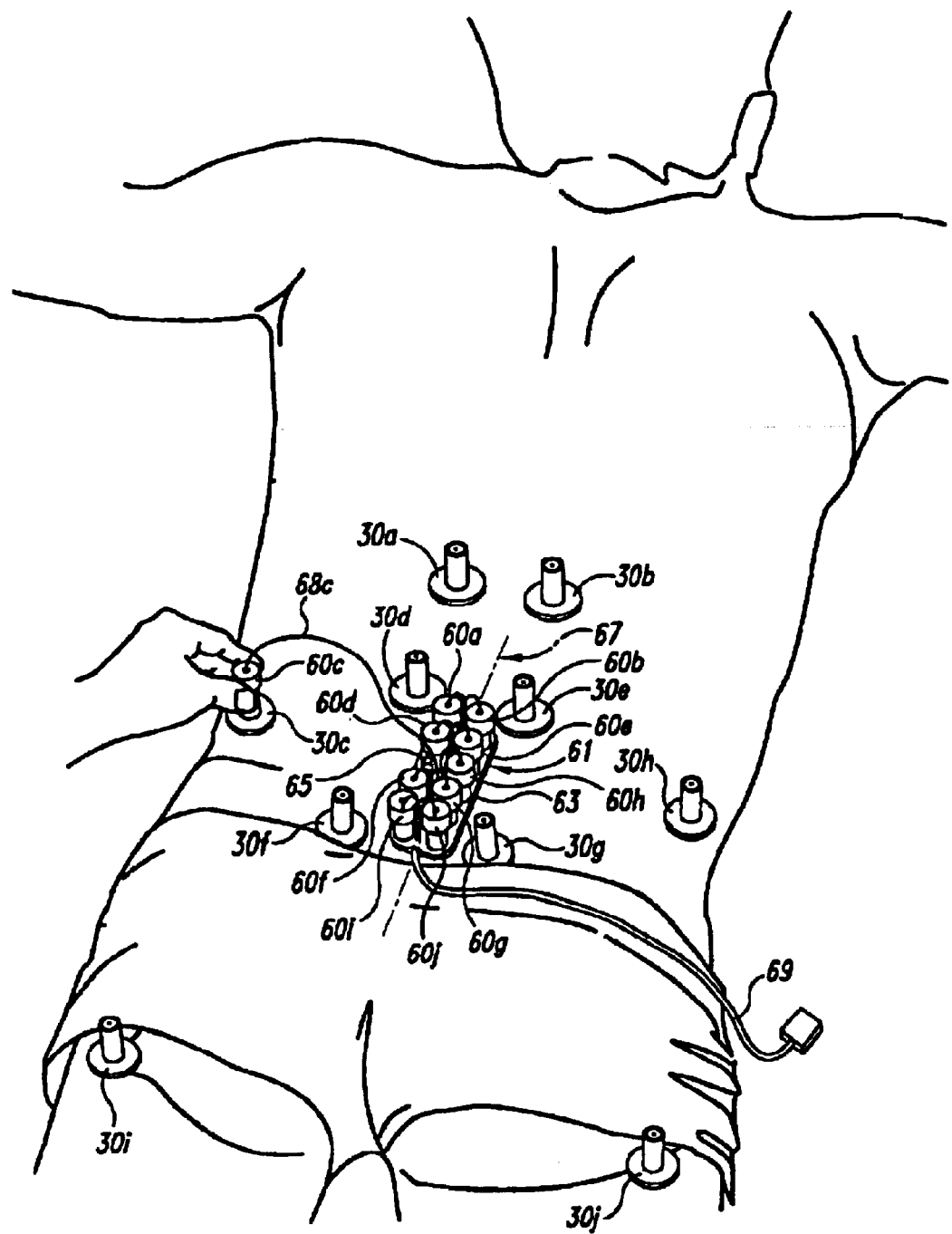
FIG. 11 shows the electrode montage of FIG. 10 at the beginning of the electrode insertion step.
Figure 12:
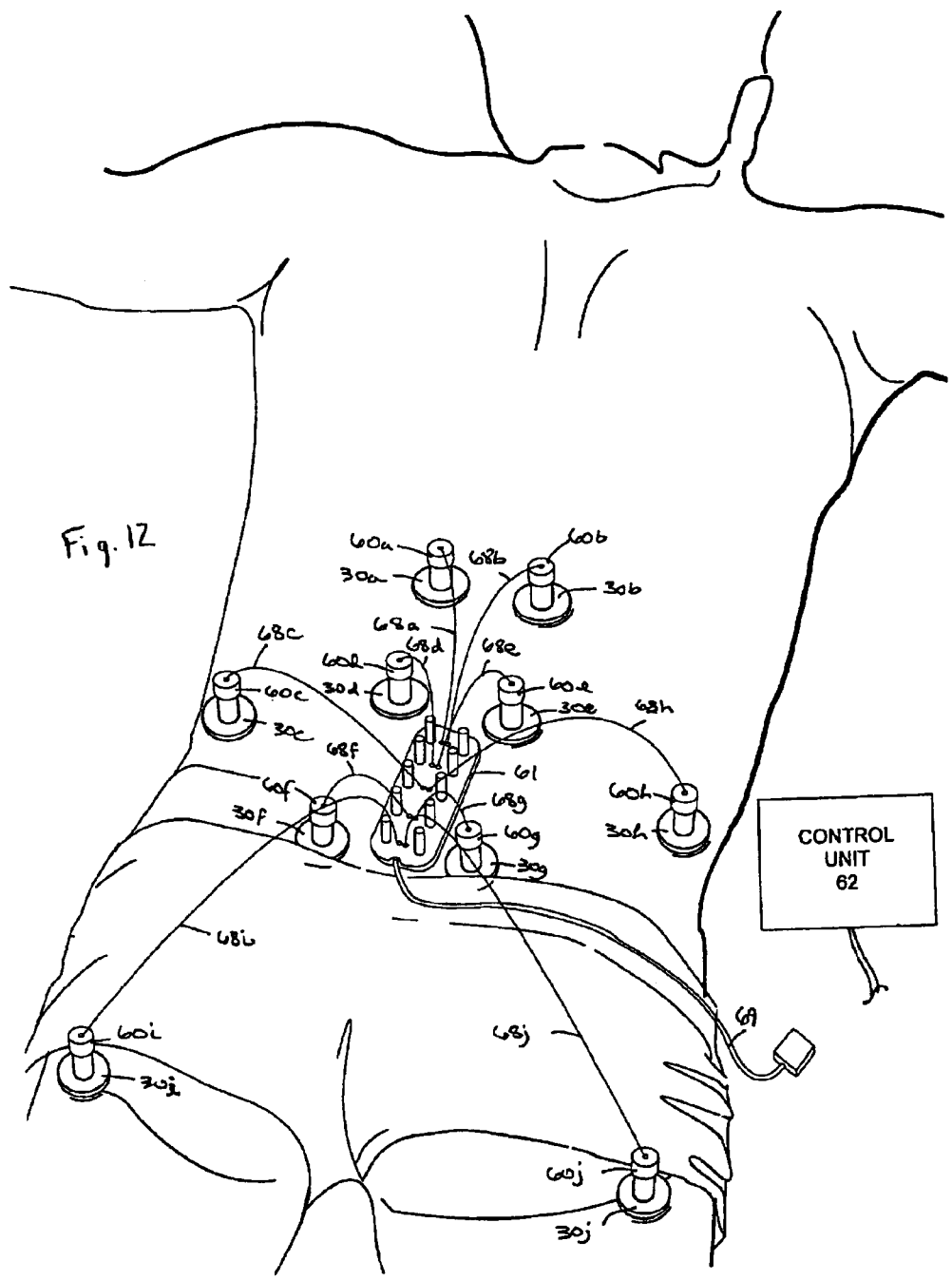
FIG. 12 shows the electrode montage of FIG. 10 with the electrodes deployed, inserted and attached to a control unit to provide electrical therapy to the patient.
Figure 13:
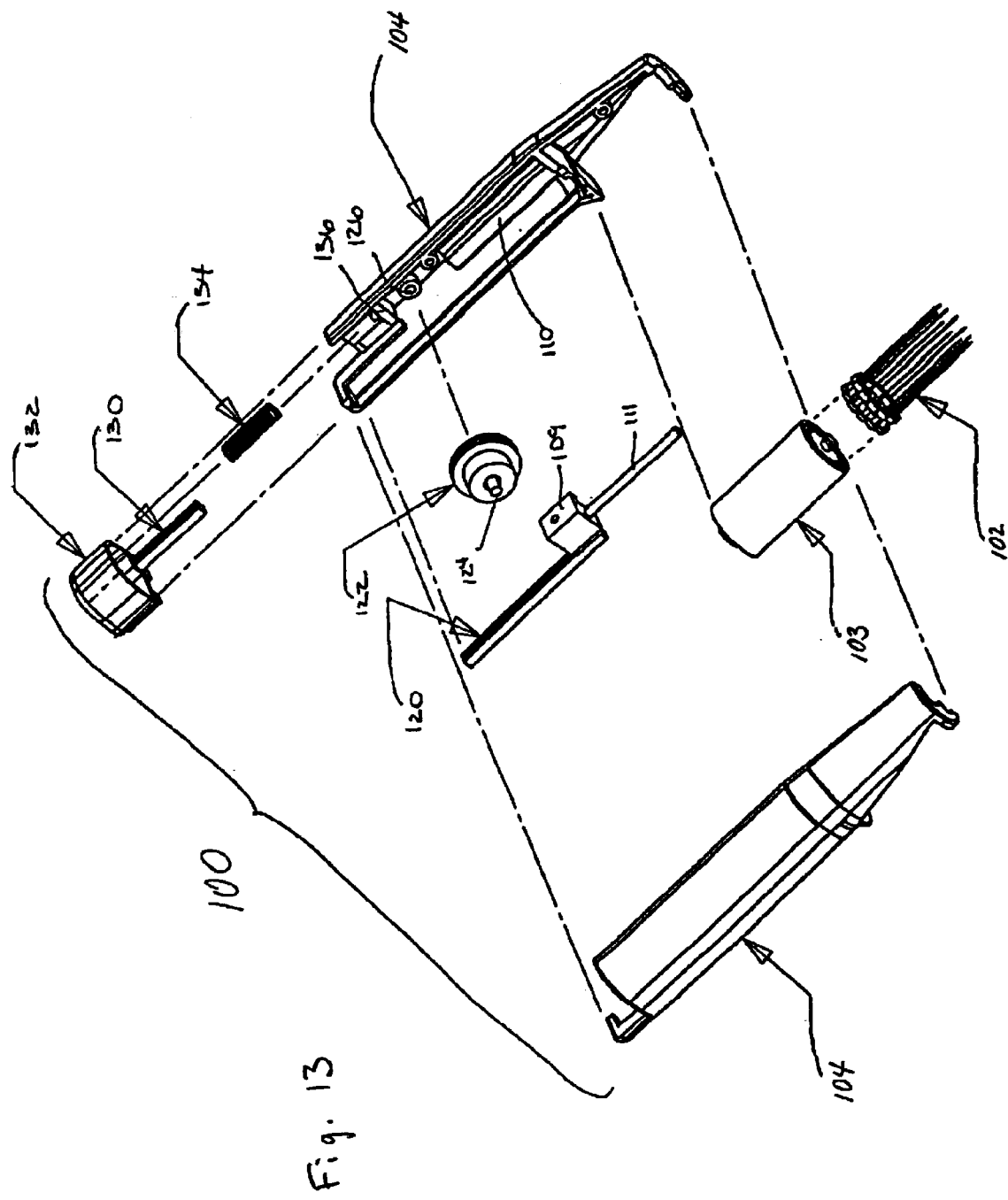
FIG. 13 is an exploded view of an electrode introducer and angle of insertion assembly of yet another embodiment of this invention.
Figure 16:
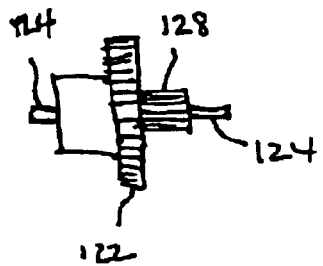
FIG. 16 is an elevational view of gear assemblies of the introducer and angle of insertion assembly of FIG. 13.

FIGS. 10–12 show the use of the electrode and sharp point protection assemblies of FIGS. 4–9 to treat low back pain using PNT. As shown in FIG. 10, ten electrode assemblies 30a–j are arranged in a montage on the patient's back and attached with adhesive. Next, ten couplers 60a–j are attached to the ten electrode assemblies 30a–j. In one embodiment (shown in FIG. 11), the couplers 60a–j are supported or carried prior to deployment by a coupler support 61 (FIG. 12). In one aspect of this embodiment, the coupler support 61 can include a generally flat, rigid support member 63 having ten engagement members 65 positioned at corresponding coupler locations of the support member 63. Each engagement member 65 can be configured to removably support or carry one of the couplers 60. For example, each engagement member 65 can include a post projecting upwardly from the support member 63 to be removably received in a corresponding axial aperture of the coupler 60. As shown in FIG. 12, each coupler 60 can be connected to the support member 63 with an individual cable 68a–j. The individual cables 68a–j can be bundled together to form a link 69 (such as a multi-wire cable) that provides electrical communication between the couplers 60 and a control unit 62.

In another aspect of this embodiment, an arrangement of the engagement members 65 on the support member 63 can correspond to an arrangement of the electrode assemblies 30a–j on the patient's back. For example, when the electrode assemblies 30a–j are connected to the patient at ten sites arranged in two rows on each side of the patient's spine, the engagement members 65 can be arranged in two rows, one on each side of a central axis 67 (FIG. 11) that can be aligned with the patient's spine. Accordingly, the arrangement of the engagement members 65 can guide the practitioner to connect each coupler 60 to the proper electrode assembly 30. Because each electrode assembly 30 is paired with another to define a complete electrical circuit (with one electrode serving as an anode and an adjacent electrode serving as a cathode), it can be important to correctly match the individual cable 68 with the corresponding electrode assembly. For example, if a given electrode assembly 30 serving as an anode is inadvertently placed too distant from the corresponding electrode assembly 30 serving as a cathode, the current applied to the electrode assemblies may be too weak to be effective. Furthermore, when the characteristics of the electrical signals supplied to each circuit are controlled separately, it may not be clear which circuit is being controlled if the couplers 60 are attached to the wrong electrode assemblies. Accordingly, the coupler support 61 can increase the effectiveness of the electrical stimulation therapy by reducing the likelihood that the couplers 60 will be incorrectly deployed. In other embodiments, the coupler support 61 can have other configurations and can support couplers having other configurations, as described below with reference to FIGS. 23–30.

Once each electrode assembly 30 has been actuated by its respective coupler 60 to insert an electrode into the patient's tissue (as shown in FIG. 12), the control unit 62 provides electrical signals to treat the patient. As described above, half the electrodes (e.g., assemblies 30b, 30d, 30g, 30h and 30i) can serve as anodes, and the other half as cathodes. In one embodiment, the control unit 62 can provide a current-regulated and current-balanced waveform with an amplitude of up to approximately 20 mA, frequency between approximately 4 Hz and 50 Hz, and pulse width of between approximately 50 $\mu$sec and 1 msec. to treat the patient's low back pain using PNT.

FIGS. 13–22 illustrate an apparatus in accordance with another embodiment of the invention. In one aspect of this embodiment, an electrode introducer and an alignment member mounted on the patient's skin provide an electrode angle of insertion assembly controlling the electrode's angle of entry into the patient's tissue. In a further aspect of this embodiment, an electrode introducer 100 shown in FIGS. 13–16 and 19–21 can insert multiple electrodes. It should be understood that the principles of this invention could be applied to an introducer designed to hold and insert any number of electrodes.

Twelve electrodes 102 are disposed within a magazine 103 rotatably mounted within a housing 104. In one embodiment, the housing 104 is a two-part injection molded polystyrene assembly. As shown in FIG. 14, the magazine 103 rotates about a hub 105 mounted on supports formed in housing 104. A leaf spring 106 mates with one of twelve radial grooves 108 formed in the magazine 103 to form a twelve-position ratchet mechanism for the rotatable magazine 103 in the housing 104.

The magazine 103 can have twelve electrode chambers 115 arranged radially about the hub 105. When the introducer 100 is completely full, each chamber 115 contains one electrode 102. The diameter of an upper portion 118 of the chamber 115 is sized to form an interference fit with the wider portions 112 and 114 of electrode handle portion 107 of electrode 102. A lower wide portion 114 of electrode 102 can be formed from a compressible material. The diameter of a lower portion 119 of the chamber 115 is slightly larger so that there is no interference fit between the lower portion 119 and the electrode handle 107, for reasons explained below. Each time the leaf spring 106 is within a groove 108, the opening 106 of a magazine chamber 115 is lined up with the aperture 117 of the introducer 100, as shown in FIGS. 14 and 15.

A slide member 109 is disposed on a rail 110 formed in the housing 104. Extending longitudinally downwardly from the slide member 109 is a drive rod 111, and extending longitudinally upwardly from the slide member 109 is a gear rack 120. The teeth of the gear rack 120 cooperate with the teeth on a rotational gear 122 mounted about a shaft 124 extending into a shaft mount 126 formed in the housing 104. A second set of teeth are mounted on a smaller diameter rotational gear 128 (shown more clearly in FIG. 16) which is also mounted about the shaft 124. The gears 122 and 128 rotate together about the shaft 124.

The teeth of the smaller diameter gear 128 mesh with the teeth of a second gear rack 130 extending from a longitudinally-movable actuator 132. A spring 134 mounted between the actuator 132 and a spring platform 136 biases the actuator 132 away from the housing 104.

To deploy the electrode assembly of this embodiment, a flexible and compressible annular patch 140 is placed on the patient's skin at the desired site, preferably with an adhesive (not shown). For example, to treat low back pain using PNT, the arrangement or montage shown in FIG. 17 may be used. In this montage, five electrodes serve as cathodes and five serve as anodes.

As shown in FIGS. 19 and 20, the patch 140 has an annular rigid member 141 disposed in its center and extending upwardly from it. The rigid member 141 has a smaller diameter opening 142 leading to a larger diameter opening 144. The diameter of the opening 142 is slightly smaller than the lower wide portion 114 of the handle portion 107 of the electrode 102 and slightly larger than the diameter of the central portion 113 of handle portion 107 of the electrode 102.

Figure 18:
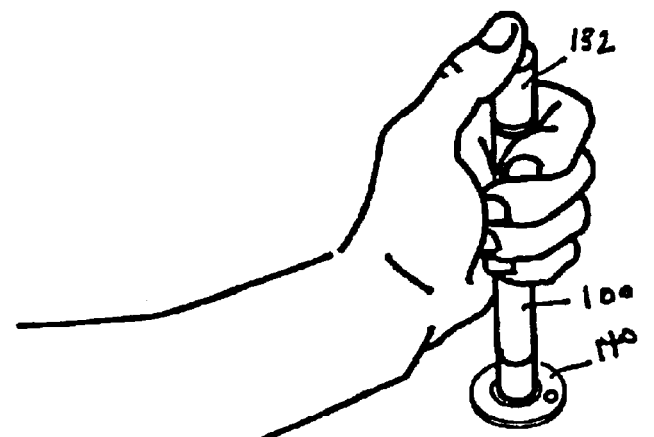
FIG. 18 is an elevational view showing the introducer of FIG. 13 in the process of deploying an electrode.

After the patch 140 is in place, the distal end of the introducer 100 is placed against the patch 140 so that the introducer aperture 117 surrounds the upwardly extending portion of rigid patch member 141, as shown in FIG. 18. This interaction aligns the opening 116 of one of the introducer's magazine chambers 115 with the opening 142 of the rigid member 141 and helps control the electrode's angle of entry, as shown in FIG. 19. Downward pressure on the introducer 100 compresses the patch 140, thereby causing the upper surface of the rigid member 141 to engage a lower surface of the magazine 103, and pressing the rigid member 141 downward into the patient's skin 22. This pressure on the patient's skin around the insertion site can reduce the pain caused by inserting the electrode.

Depressing the actuator 132 moves the gear rack 130 distally, which causes the gears 128 and 122 to rotate. Because the diameter and tooth count of the gear 128 differ from the diameter and tooth count the gear 122, the gear rack 120 moves longitudinally a much greater distance than the corresponding longitudinal movement of the gear rack 130. This feature enables the electrode to be inserted its required distance into the patient's skin using only a comparatively small movement of the operator's thumb. Distal movement of the gear rack 120 is guided by the movement of the slide member 109 along the rail 110.

As the slide member 109 moves distally, the drive rod 111 moves into a magazine chamber 115 until the distal end of the drive rod 111 engages the top surface of the electrode's handle portion 107. As shown in FIG. 20, further distal movement of the drive rod 111 pushes the electrode 102 downwardly so that the sharp point 108 of the electrode 102 leaves the introducer housing and enters the patient's skin 22 and the tissue beneath the skin. The chamber 115 provides axial stability to the electrode 102 during insertion.

When the top portion 112 of the electrode handle portion 107 leaves the smaller diameter portion 118 of the magazine chamber 115, it enters the larger diameter portion 119 of the chamber 115. At this point (shown in FIG. 21), because the diameter of chamber portion 119 is wider than the diameter of the electrode handle 107, the electrode is no longer attached to the introducer 100.

Continued downward movement of the actuator 132 and the drive rod 111 pushes the lower larger diameter portion 114 of the electrode handle 107 through the smaller diameter portion 142 of rigid member 141 by compressing the handle portion 114. Further downward movement pushes the handle portion 114 into the larger diameter portion 144 of the rigid member 141 so that the rigid member's smaller diameter portion lies between the larger diameter portions 112 and 114 of the electrode handle 107. This interaction holds the electrode in place in the patient's tissue and helps provide depth control for electrode insertion. In this embodiment, the preferred depth of the electrode's sharp point 108 is approximately 3 cm, although the electrode may be inserted to other depths depending on the treatment to be performed. The slider member 109 also acts as a limit stop at this point when it engages the limit stop area 145 of housing 104, thereby also controlling electrode insertion depth.

Figure 22:
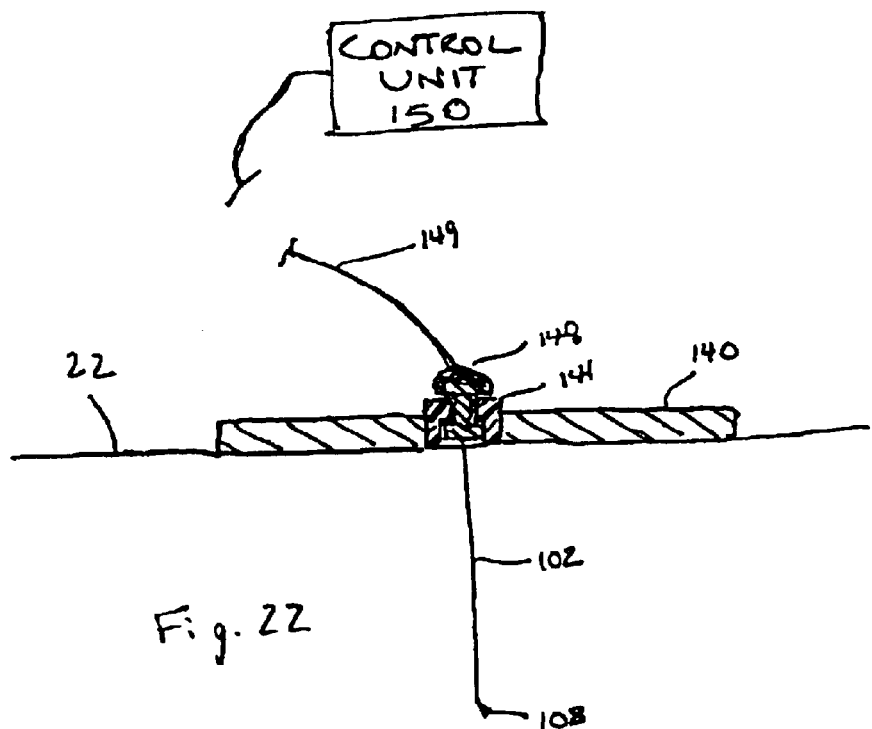
FIG. 22 is a sectional view of an inserted electrode assembly of the embodiment of FIGS. 13–16.

The magazine 103 can be rotated to a new insertion position and placed against an empty patch 140 after insertion of each electrode until all electrodes have been deployed and inserted. A suitable electrical connector 148, such as an alligator clip, can be electrically connected to electrode 102 through an aperture (not shown) formed in the upper larger diameter portion 112 of electrode handle 107 to provide electrical communication between a control unit 150 and electrode 102 via a cable or other conductor 149, as shown in FIG. 22. The patch 140 can provide strain relief for the electrode 102 by preventing tugging forces on the cable 149 from dislodging the electrode from the patient, thereby helping keep the electrode in place. In one aspect of this embodiment, the sharp point of the electrode is not exposed to the operator or bystander at any point during the electrode deployment, insertion and electrical therapy treatment processes.

The control unit 150 supplies stimulation current to the electrodes, e.g., in the manner described in the Ghoname et al. articles. Once again, the electrical waveform provided by the control unit depends on the application. For example, in an embodiment of a system providing percutaneous neuromodulation therapy, the control unit 150 can provide a current-regulated and current-balanced waveform with an amplitude of up to approximately 20 mA, frequency between approximately 4 Hz and 50 Hz, and pulse width of between approximately 50 $\mu$sec and 1 msec.

In an alternative embodiment, the lower wide portion of the electrode handle can be formed from a rigid material and can have rounded camming edges. The central annulus of patch 140 in this alternative embodiment is either compressible or has a resilient camming opening under the camming action of the electrode handle.

Figure 23:
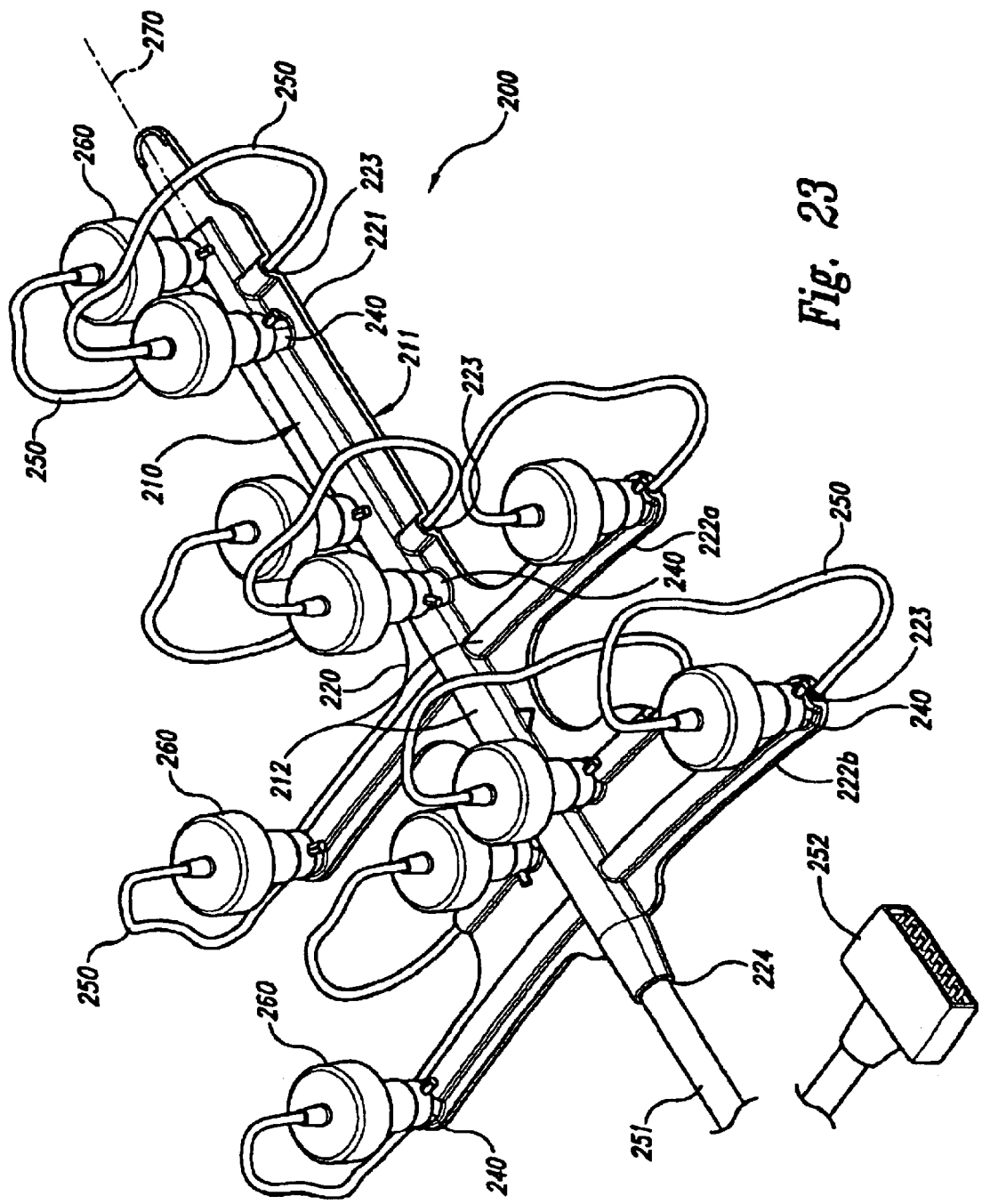
FIG. 23 is a partially schematic, top isometric view of a coupler support in accordance with an embodiment of the invention.

FIG. 23 is a top isometric view of a coupler support 200 that supports or carries couplers 260 in accordance with another embodiment of the invention. In one aspect of this embodiment, the coupler support 200 includes a support member 220 and ten engagement members 240 positioned at coupler locations of the support member 220. Each engagement member 240 can removably support one of the couplers 260. In one aspect of this embodiment, the couplers 260 can be generally similar to the coupler 60 described above with reference to FIGS. 4–12. Alternatively, the coupler 260 can have other configurations, such as the configuration disclosed in co-pending U.S. application Ser. No. 09/666,931, entitled "Method and Apparatus for Repositioning a Percutaneous Probe," incorporated above by reference. In other embodiments, the coupler can have other configurations, for example, those described below with reference to FIGS. 27–30.

When the couplers 260 are generally similar to the couplers 60 described above with reference to FIGS. 4–12, each engagement member 240 can have columnar or post shape and can be removably received in a downward facing aperture of the coupler 260. The engagement member 240 can extend a sufficient distance upwardly into the aperture of the coupler 260 to fly support the coupler 260 relative to the support member 220. In other embodiments, the engagement member 240 can have other configurations (for example, when the coupler has other configurations), as described below with reference to FIGS. 26–30.

The coupler support 200 can include links 250 between the support member 220 and each coupler 260. In one aspect of this embodiment, the links 250 can include electrical cables to transmit electrical signals to the couplers 260 and to the patient or recipient to whom the couplers 260 are attached. In other embodiments, the links 250 can have other configurations, as described below with reference to FIGS. 27–30. In any of these embodiments, different links 250 can have different lengths to allow the corresponding coupler 260 to be coupled to the appropriate site on the recipient. Alternatively, each link 250 can have the same length, so long as the length is sufficient for each coupler 260 to be coupled to the proper site on the recipient. For example, in one embodiment, a single support member 220 with a single set of links 250 can be compatible with recipients ranging in height from about 4.5 feet to about 6.5 feet.

When the links 250 include electrical cables, each link 250 can enter the support member 220 at an entry attachment point 223. The links 250 can then pass through a cable channel 212 of the support member 220 and exit the support member 220 at an exit attachment point 224. The links 250 can be bundled together to form a bundled link 251 that can be attached to an electrical connector 252 for coupling to a source of electrical potential.

In one embodiment, the support member 220 can include an upper portion 210 bonded to a lower portion 211. The upper portion 210 can include the cable channel 212 and the engagement members 240. The support member 220 can be formed by molding the upper portion 210, inverting the upper portion 210, and laying a cable harness (which includes the bundled link 251 and the individual links 250) into the cable channel 212. The lower portion 211 can be attached to the upper portion 210 (for example, in an overmold process) to fix the harness into the support member 220. In other embodiments, the coupler support 200 can be formed with other techniques. In any of these embodiments, the support member 220 can include a flexible, soft durometer, bio-compatible, thermoplastic elastomeric material, such as Sanoprene®, available from Advanced Elastomeric Systems of Akron, Ohio. Accordingly, the support member 220 can conform to the shape of the recipient's body, as described below with reference to FIG. 24.

In a further aspect of this embodiment, the shape of the support member 220 and the positions of the engaging members on the support member 220 can be configured to aid the practitioner in connecting each coupler 260 to the correct corresponding coupling site on the recipient's body. For example, when the coupler support 200 is configured to administer electrical therapy to the recipient's back, the support member 220 can have an axial elongated portion 221 aligned with a central axis 270. The support member 220 can further include two transverse elongated portions 222 (shown as a first transverse elongated portion 222a and second transverse elongated portion 222b) arranged transverse to the central axis 270. In one aspect of this embodiment, the coupler support 200 generally and the elongated portions 221, 222 in particular can be configured to be spaced apart from corresponding coupling sites on the recipient's back, so as not to interfere with the operation of attaching the couplers 260 to the recipient. For example, in one embodiment, the axial elongated portion 221 can have a length of about 11 inches ±0.25 inch (measured from the exit attachment point 224). The transverse elongated portions 222a, 222b can have lengths of about 6.8 inches and about 7.5 inches, respectively, ±0.25 inch. In other embodiments, the elongated portions 221, 222 can have other dimensions. In any of these embodiments, each coupler 260 can be positioned proximate to its corresponding coupling site to aid the practitioner in connecting the couplers with the appropriate coupling site, as described below with reference to FIG. 24.

Figure 24:
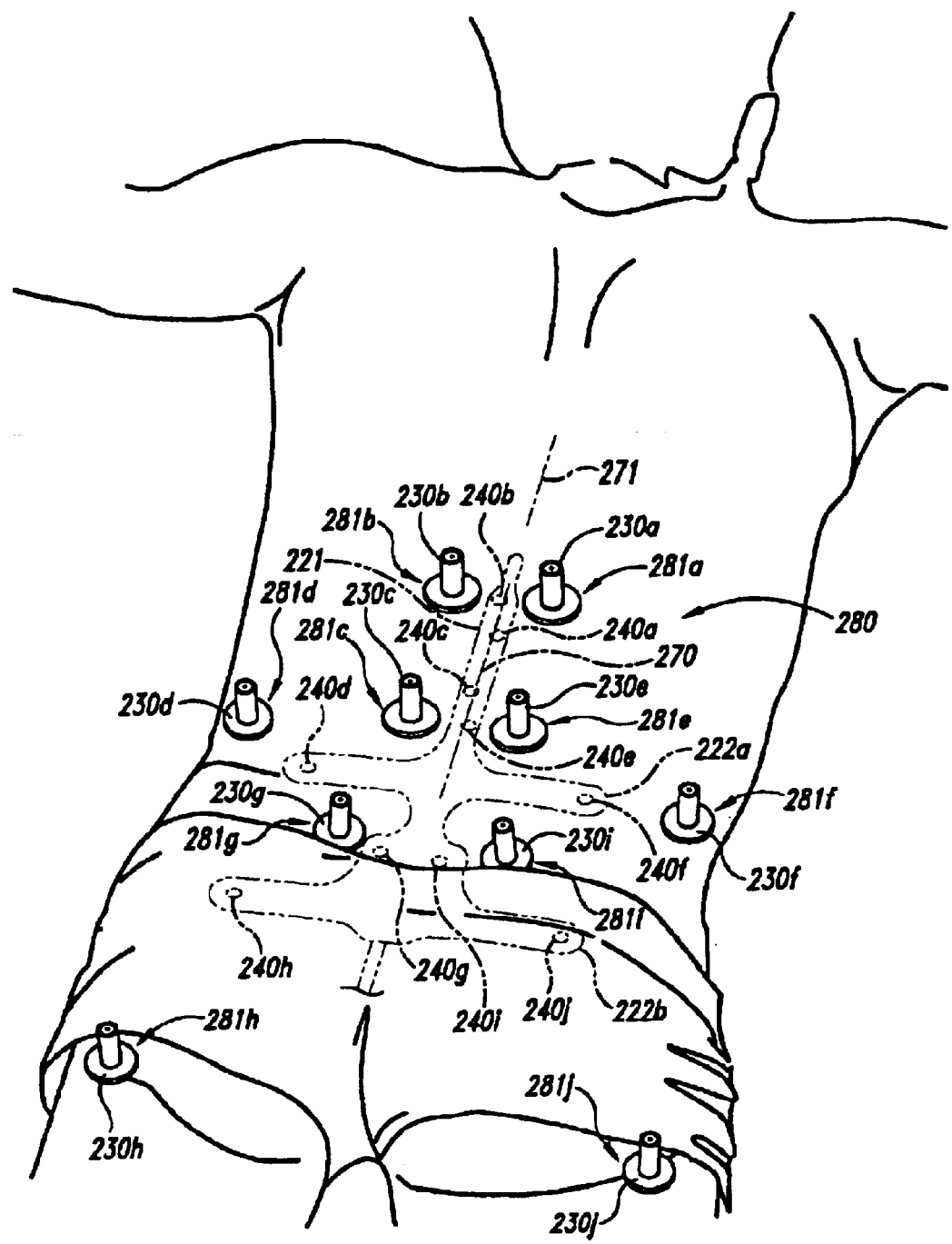
FIG. 24 is a partially schematic, top isometric view of a coupler support positioned on the back of a recipient in accordance with another embodiment of the invention.

FIG. 24 is a partially schematic, top isometric view of the coupler support 200 (shown in phantom lines) placed in position on the back of a recipient. For purposes of clarity, the coupler support 200 is shown schematically in FIG. 24 without the couplers 260. In one aspect of this embodiment, the central axis 270 of the coupler support 200 is aligned with a body longitudinal axis 271 (such as the spine) to position the coupler support 200 proximate to a coupling area 280 on the recipient. The coupling area can be on the recipient's back (as shown in FIG. 24) or, alternatively the coupling area can be on the recipient's neck, head, leg or other body part. When the coupler support 200 is in position on the coupling area 280, the elongated portions 221, 222a and 222b can flex to conform to the shape of the recipient's body in the coupling area 280. Accordingly, the coupler support 200 can be less likely to be dislodged from the recipient's body and can more accurately align the couplers 260 with the appropriate portions of the coupling area 280.

The coupling area 280 includes a plurality of coupling positions or sites 281 (shown as 281a–j) at which a corresponding plurality of electrode assemblies 230 (shown as 230a–j) are attached. In one embodiment, the electrode assemblies 230 are arranged in cathode/anode pairs with five circuits formed by electrode assembly pairs 230a and 230b; 230c and 230d; 230e and 230f, 230g and 230h; and 230i and 230j. Once the coupler support 200 is in position on the recipient's back, each engagement member 240 (shown as 240a–j) is positioned proximate to its corresponding electrode assembly 230a–j. For example, those engagement members 240 that are to be coupled with electrode assemblies 230 close to the body longitudinal axis 271 are positioned close to the central axis 270 of the coupler support 200. Those engagement members 240 that are to be coupled with electrode assemblies 230 further away from body longitudinal axis 271 are positioned further away from the central axis 270 of the coupler support 200. Accordingly, many of the couplers 260 are positioned closer to the one corresponding electrode assembly 230 to which that coupler 260 is to be connected than to any other electrode assembly. As a result, practitioners will be less likely to link the couplers 260 to the incorrect electrode assembly 230.

Figure 25:
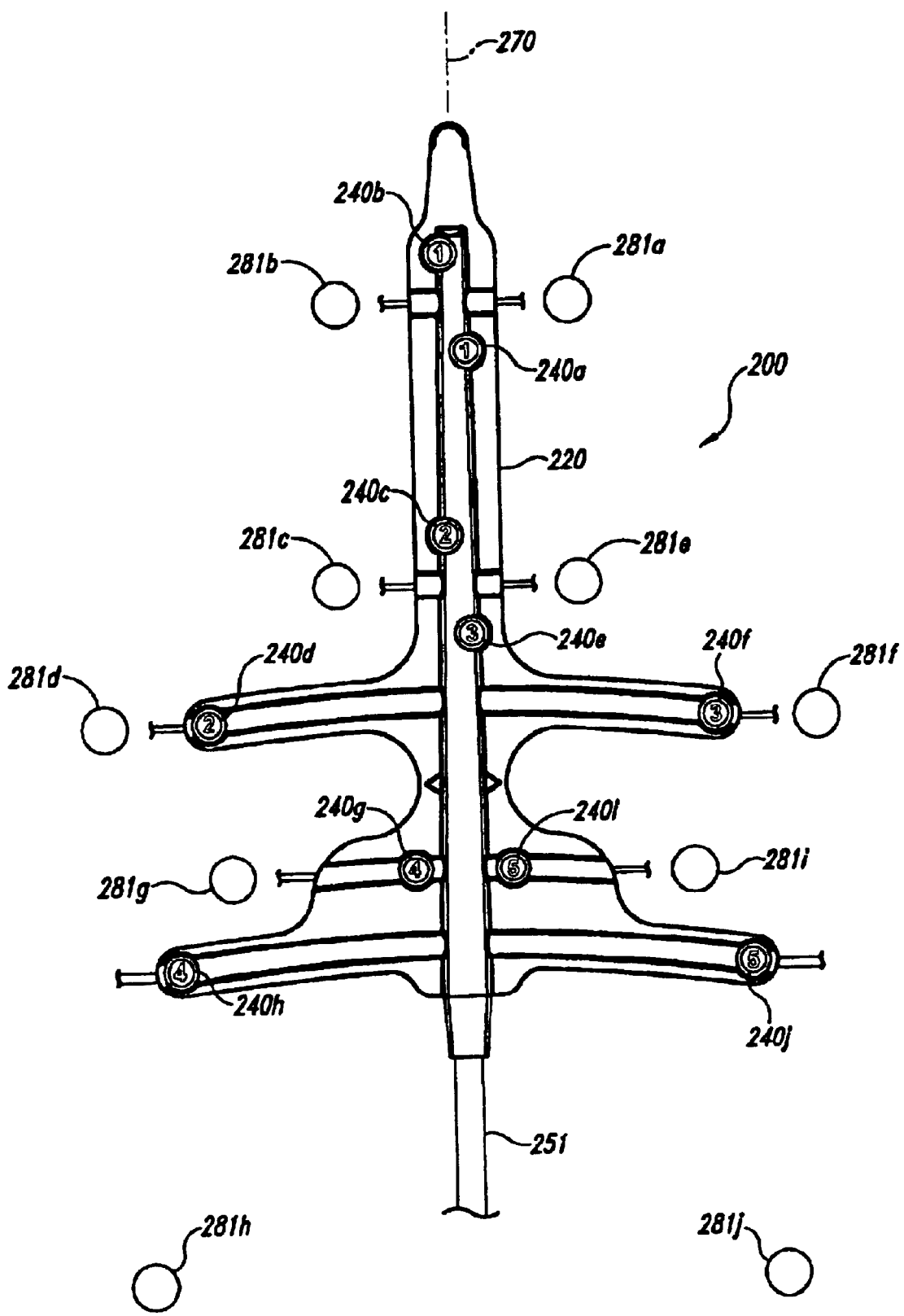
FIG. 25 is a partially schematic, top plan view of a support member positioned near coupling positions in accordance with another embodiment of the invention.

FIG. 25 is a top plan view of the coupler support 200 with the couplers 260 removed so that the tops of the engagement members 240a–j are visible. In one aspect of this embodiment, the engagement members 240a–j can be marked to indicate which circuit the corresponding couplers 260 are connected to. For example, the engagement members 240a and 240b can be marked with a numeral "1" to indicate that the couplers 260 removed from these engagement members are connected to the recipient to form circuit number "1." An advantage of this arrangement is that if the control unit 62 (FIG. 9) indicates that circuit number "1" is faulty or defective, the practitioner can easily narrow the field of potentially faulty couplers 260 to the two couplers 260 removed from engagement members 240a and 240b.

In another aspect of this embodiment, the coupler support 200 can include other features to further aid the practitioner in attaching the couplers 260 to the correct coupling site 281. For example, the engagement member 240a can be can be offset to the right side of the central axis 270 and the engagement member 240b can be offset to the left side of the central axis 270 so that the practitioner will be more likely to connect the corresponding couplers 260a, 260b (FIG. 24) to the appropriate coupling site 281a, 281b. In a further aspect of this embodiment, the engagement members 240a, 240e, 240f, 240i and 240j positioned on the right side of the central axis 270 can have a different color than the engagement members 240b, 240c, 240d, 240g and 240h positioned on the left side of the central axis 270. As is also shown in FIGS. 24 and 25, the overall shape of the coupler support 200, and in particular, an outline defined by the positions of the engagement members 240, is generally similar to an outline defined by the positions of the coupling sites 281. In other embodiments, for example, when the coupler support 200 is configured to rest on the recipient's leg, neck or head for therapy to these regions, the outline defined by the engagement members can also correspond to the outline defined by the coupling sites. In any of these embodiments, the relative longitudinal and lateral locations of the engagement members 240 can correspond at least roughly with the relative longitudinal and lateral locations of the coupling sites 281 on the recipient's body.

FIG. 26 is a top isometric view of a portion of a coupler support 300 having a transverse elongated portion 322a with an engagement member 340 in accordance with another embodiment of the invention. The overall shape of the coupler support 300 can be generally similar to that described above with reference to FIGS. 23–25. In one aspect of this embodiment, the engagement member 340 can include an aperture 341 positioned to receive the housing of a coupler, such as the coupler 260 described above with reference to FIG. 23 or the coupler 60 described above with reference to FIGS. 4–8. In still a further aspect of this embodiment, the engagement member 340 can include a pair of entrance slots 342 positioned to receive the pegs 70 (FIG. 5) of the coupler 60. Once the pegs 70 have been moved into the entrance slots 342, the coupler 60 can be rotated clockwise to move the pegs 70 into transverse locking slots 343. Accordingly, an advantage of this arrangement is that it can securely, yet removably, engage the coupler 60.

FIG. 27 is a top isometric view of a portion of a coupler support 400 having a transverse elongated portion 422a with an engagement member 440 in accordance with another embodiment of the invention. In one aspect of this embodiment, the engagement member 440 can include an aperture 441 configured to receive a clamping coupler 460, such as an alligator clip. The clamping coupler 460 can be attached directly to a percutaneous acupuncture needle 402 or another percutaneous or transcutaneous device. When the clamping coupler 460 is not attached to the needle 402, it can be removably positioned in the aperture 441 while remaining connected to an electrical link 450, such as a cable. In an alternate arrangement shown in FIG. 28, the coupler support 400 can include an engagement member 440a having a post shape. In one aspect of this embodiment, the clamping coupler 460 can be clamped to the engagement member 440a to support the coupler 460 relative to the coupler support 400.

In one aspect of the embodiments described above with reference to FIGS. 27 and 28, the clamping coupler 460 can be attached to a percutaneous electrode, such as the electrode 102 described above with reference to FIG. 22. Alternatively, the coupler 460 (or other couplers) can be attached to a transcutaneous electrical nerve stimulation system. In still a further embodiment (shown in FIG. 29), a clamping coupler 660 can be clamped to a diagnostic electrode, such as a patch electrode or an EMG needle electrode 630 of the type available from SLE of South Croydon, England. A plurality of the couplers 660 (one of which is shown in FIG. 29) can be connected to a support 600 (shown schematically in FIG. 29) in a configuration generally similar to that described above with reference to FIG. 23 and/or FIG. 11. The support 600 can be connected with a bundled link 651 to a care unit 690. The care unit 690 can include a diagnostic instrument that receives electrical signals from the coupler 660, rather than providing electrical signals to the coupler 660. Accordingly, the support 600 can aid the practitioner in coupling the plurality of couplers 660 to the correct corresponding electrode 630.

FIG. 30 is a partially schematic view of a coupler support 700 that can aid the practitioner in delivering medicament to a plurality of coupling sites on the recipient in accordance with another embodiment of the invention. Accordingly, the coupler support 700 can include a plurality of medicament links 750 (one of which is shown in FIG. 30), such as a length of drug delivery tubing. Each link 750 can include a coupler 760 for attaching to a needle or other drug delivery device 730 inserted into the recipient. The individual medicament links 750 can be bundled together to form a bundled link 751 which is connected to a care unit 790. The care unit 790 can include a pump, drip bag, or other arrangement for providing liquid medicament to the coupler support 700 and the recipient.

A feature of embodiments of the coupler support arrangements described above with reference to FIGS. 11 and 23–30 is that the supports are configured to position the couplers proximate to the appropriate coupling location. Accordingly, practitioners, including relatively inexperienced practitioners, can be less likely to connect the couplers to an incorrect coupling location. An advantage of this arrangement is that the couplers can provide more reliable and/or more efficacious therapy and/or diagnostic information. A further advantage is that the practitioner can more quickly connect the couplers to the recipient, increasing the efficiency with which the practitioner can provide therapy and/or diagnostic information.

Still a further advantage of embodiments of the coupler support described above is that a single support can accommodate a wide variety of applications. For example, a single support can be used with recipients ranging in height from about 4.5 feet to about 6.5 feet, as discussed above. A single coupler support can also be used with recipients having a wide variety of body shapes. Still further, a single coupler support can be positioned on recipients having a variety of postures. For example, a single coupler support can rest on the recipient's back whether the recipient is prone, leaning over, or partially upright, while still allowing the couplers to be connected to the appropriate coupling locations.

From the foregoing, it will be appreciated that, although specific embodiments of the invention have been described herein for purposes of illustration, various modifications may be made without deviating from the spirit and scope of the invention. For example, the couplers can be connected directly to the recipient rather than being connected to an intermediate device such as an electrode (i.e., the electrode can be integrated with the coupler). The coupler locations of the support member can include posts or columns, apertures, or any other feature that removably carries the couplers. Accordingly, the invention is not limited except as by the appended claims.

What is claimed is:

1. An apparatus for supporting couplers for removable coupling to a recipient during at least one of therapy administration and recipient monitoring, the apparatus comprising:

a first coupler having an electrical contact configured to be connected to a percutaneous electrical probe inserted into the recipient;

a support member, which aids in placement of the couplers, configured to rest on a body of the recipient proximate to a coupling region, the support member having a first engagement portion configured to be positioned proximate to a first coupling position on the body of the recipient and a second engagement portion configured to be positioned proximate to a second coupling position on the body of the recipient;

a first engagement member configured to removably carry the first coupler at the first engagement portion of the support member;

a second engagement member configured to removably carry a second coupler at the second engagement portion of the support member, the first engagement member configured to be positioned closer than the second engagement member to the first coupling position; and a flexible cable connected between the first coupler and the support member, the cable remaining connected between the first coupler and the support member when the first coupler is moved from a first attached position with the first coupler carried by the first engagement member to a first coupled position with the first coupler operatively coupled to the recipient, wherein the first coupler includes an actuator tool configured to insert the percutaneous electrode in the recipient, and wherein the first engagement member is configured to carry the first coupler including the actuator tool.

2. An apparatus for supporting a plurality of percutaneous probe couplers in position for removable coupling to a recipient, comprising:

a flexible support member, which aids in placement of the couplers configured to rest on a body of a recipient and conform to a curvature of the body proximate to a location where the couplers are to be coupled to the body, wherein the support member has a central axis, a first elongated portion positioned along the central axis, a second elongated portion extending transversely to the central axis on first and second sides of the central axis, and a third elongated portion positioned between the first and second elongated portions and extending transversely to the central axis on the first and second sides of the central axis, further wherein the first and second engagement members are positioned on one of the elongated portions, with the first engagement member including a column positioned on the first side of the central axis and the second engagement member including a column positioned on the second side of the central axis;

a first engagement member depending from the support member and configured to be positioned proximate to a first coupling position on the body;

a first coupler removably engaged with the first engagement member wherein the first coupler includes an actuator tool configured to insert a percutaneous electrode in the recipient;

a first electrical cable attached between the first coupler and the support member;

a second engagement member depending from the support member and configured to be positioned proximate to a second coupling position on the body of the recipient, the first engagement member configured to be positioned closer than the second engagement member to the first coupling position, the second engagement member configured to be positioned closer than the first engagement member to the second coupling position;

a second coupler removably engaged with the second engagement member; and a second electrical cable attached between the second coupler and the support member.

3. An apparatus for supporting a plurality of percutaneous probe couplers in position for removable coupling to a recipient, comprising:

a flexible support member which aids in placement of the couplers, configured to rest on a body of a recipient and conform to a curvature of the body proximate to a location where the couplers are to be coupled to the body, wherein the support member has a central axis, a first elongated position positioned along the central axis, a second elongated portion extending transversely to the central axis on the first and second sides of the central axis, and a third elongated portion positioned between the first and the second elongated portions and extending transversely to the central axis on the first and second sides of the central axis, further wherein the first and second engagement members are positioned on one of the elongated portions, with the first engagement member including a column positioned on the first side of the central axis and the second engagement member including a column positioned on the second side of the central axis;

a first engagement member depending from the support member and configured to be positioned proximate to a first coupling position on the body;

a first coupler removably engaged with the first engagement member;

a first electrical cable attached between the first coupler and the support member, a second engagement member depending from the support member and configured to be positioned proximate to a second coupling position on the body of the recipient, the first engagement member configured to be positioned closer than the second engagement member to the first coupling position, the second engagement member configured to be positioned closer than the first engagement member to the second coupling position;

a second coupler removably engaged with the second engagement member; and a second electrical cable attached between the second coupler and the support member.

4. An apparatus for supporting a plurality of percutaneous probe couplers in position for removable coupling to a recipient, comprising:

a flexible support member, which aids in placement of the couplers, configured to rest on a body of a recipient and conform to a curvature of the body proximate to a coupling location where the couplers are to be coupled to the body, the support member having a central axis;

a first engagement member depending from the support member and positioned on a first side of the central axis, the first engagement member configured to be positioned proximate to a first coupling position on the body of the recipient, the first coupling position located on the first side of the central axis;

a first coupler removably engaged with the first engagement member, wherein the first coupler includes an actuator tool configured to insert a percutaneous electrode in the recipient;

a first electrical cable attached between the first coupler and the support member;

a second engagement member depending from the support member and positioned on a second side of the central axis opposite the first side of the central axis, the second engagement member configured to be positioned proximate to a second coupling position on the body of the recipient, the second coupling position located on the second side of the central axis;

a second coupler removably engaged with the second engagement member; and a second electrical cable attached between the second coupler and the support member.

5. An apparatus for supporting a plurality of percutaneous probe couplers in position for removable coupling to a recipient, comprising:

a flexible support member, which aids in placement of the couplers, configured to rest on a body of a recipient and conform to a curvature of the body proximate to a coupling location where the couplers are to be coupled to the body, the support member having a central axis, wherein the support member has a first elongated portion positioned along the central axis, a second elongated portion extending transversely to the central axis on first and second sides of the central axis, and a third elongated portion positioned between the first and second elongated portions and extending transversely to the central axis on the first and second sides of the central axis;

a first engagement member depending from the support member and positioned on a first side of the central axis, the first engagement member configured to be positioned proximate to a first coupling position on the body of the recipient, the first coupling position located on the first side of the central axis;

a first coupler removably engaged with the first engagement member;

a first electrical cable attached between the first coupler and the support member;

a second engagement member depending from the support member and positioned on a second side of the central axis opposite the first side of the central axis, the second engagement member configured to be positioned proximate to a second coupling position on the body of the recipient, the second coupling position located on the second side of the central axis;

a second coupler removably engaged with the second engagement member; and a second electrical cable attached between the second coupler and the support member.

6. An apparatus for supporting a plurality of percutaneous probe couplers in position for removable coupling to a recipient, comprising:

a flexible support member configured to rest on a back of a recipient and conform to a curvature of the back proximate to a coupling region of the back, the support member having a central axis, a first elongated portion positioned along the central axis a second elongated portion extending transversely to the central axis on first and second sides of the central axis and a third elongated portion between the first and second elongated portions and extending transversely to the central axis on the first and second sides of the central axis;

five pairs of engagement posts depending from the support member, engagement posts of a first pair positioned on opposite sides of the central axis toward an end of the first elongated portion, engagement posts of a second pair positioned at opposite ends of the second elongated portion, engagement posts of a third pair positioned at opposite ends of the third elongated portion, engagement posts of a fourth pair positioned on opposite sides of the central axis between the first and second pair, and engagement posts of a fifth pair positioned on opposite sides of the central axis between the second and third pair;

five pairs of couplers, each coupler having an aperture with aperture walls removably engaged with one of the engagement posts; and five pairs of electrical cables with each electrical cable attached between one of the couplers and the support member.

7. The apparatus of claim 6 wherein each cable enters the support member at a separate entry point and exits the support member at a common exit point, the cables being bundled together external to the exit point and connected to a single connector.

8. The apparatus of claim 6 wherein the first coupler includes an actuator tool configured to insert a percutaneous electrode in the recipient.

9. The apparatus of claim 6 wherein the first coupler includes an electrically conductive clamp.

10. The apparatus of claim 6 wherein the first coupler includes an electrically conductive alligator clip.

11. The apparatus of claim 6 wherein the support member is configured to rest on the back of the recipient proximate to the coupling region having a plurality of coupling positions, and wherein an outline of the coupling positions defines a first shape and an outline of the engagement members defines a corresponding second shape at least generally similar to the first shape.

12. An apparatus for supporting couplers for removable coupling to a recipient during at least one of therapy administration and recipient monitoring, the apparatus comprising:

support member which aids in placement of the couplers on the recipient, and is configured to rest on a body of the recipient, the support member having a first coupler portion configured to be positioned proximate to a first coupling position of the body of the recipient, the support member further having a second coupler portion configured to be positioned proximate to a second coupling position of the body of the recipient, the first coupler portion configured to be positioned closer than the second coupler portion to the first coupling position on the body of the recipient;

a first coupler configured to be operatively coupled to the body when spaced apart from the first coupler portion and configured to be removably supported at the first coupler portion;

a second coupler configured to be operatively coupled to the body when spaced apart from the second coupler portion and configured to be removably supported at the second coupler portion;

a recipient care unit configured to deliver therapy, monitor a condition of the recipient, or delivery therapy and monitor a condition of the recipient, wherein the recipient care unit includes a source of electrical current which provides electrical stimulation to the couplers; and a first link between the care unit and the first coupler and a second link between the care unit and the second coupler.

13. An apparatus for supporting couplers for removable coupling to a recipient during at least one of therapy administration and recipient monitoring, the apparatus comprising:

support member configured to rest on a body of the recipient, the support member having a first coupler portion configured to be positioned proximate to a first coupling position of the body of the recipient, the support member further having a second coupler portion configured to be positioned proximate to a second coupling position of the body of the recipient, the first coupler portion configured to be positioned closer than the second coupler portion to the first coupling position on the body of the recipient;

a first coupler configured to be operatively coupled to the body and removably supported at the first coupler portion;

a second coupler configured to be operatively coupled to the body and removably supported at the second coupler portion;

a recipient care unit configured to deliver therapy, monitor a condition of the recipient, or delivery therapy and monitor a condition of the recipient; and a first link between the care unit and the first coupler and a second link between the care unit and the second coupler;

wherein the support member has a central axis, a first elongated portion positioned along the central axis, a second elongated portion extending transversely to the central axis on first and second sides of the central axis, and a third elongated portion positioned between the first and second elongated portions and extending transversely to the central axis on the first and second sides of the central axis, further wherein the first and second coupler locations are positioned on one of the elongated portions, with the first coupler location including a post positioned on the first side of the central axis and the second coupler location including a post positioned on the second side of the central axis.

* * * * *